(12) United States Patent
Eberlin et al.

(10) Patent No.: US 12,378,227 B2
(45) Date of Patent: Aug. 5, 2025

(54) THERAPEUTIC COCRYSTALS OF 3-{[5-(AZETIDINE-1-YLCARBONYL)PYRAZIN-2-YL]OXY}-5-{[(1S)-1-METHYL-2-(METHYLOXY)ETHYL]OXY)-N-(5-METHYLPYRAZIN-2-YL)BENZAMIDE

(71) Applicant: CONDUIT UK MANAGEMENT LTD, London (GB)

(72) Inventors: Alex Eberlin, Cambridge (GB); Christopher Frampton, Suffolk (GB); Joanne Holland, Cambridgeshire (GB)

(73) Assignee: CONDUIT UK MANAGEMENT LTD, London (GB)

( * ) Notice: Subject to any disclaimer, the term of this patent is extended or adjusted under 35 U.S.C. 154(b) by 0 days.

(21) Appl. No.: 18/688,683

(22) PCT Filed: Oct. 12, 2022

(86) PCT No.: PCT/IB2022/000775
§ 371 (c)(1),
(2) Date: Mar. 1, 2024

(87) PCT Pub. No.: WO2023/084313
PCT Pub. Date: May 19, 2023

(65) Prior Publication Data
US 2025/0011305 A1 Jan. 9, 2025

Related U.S. Application Data

(60) Provisional application No. 63/239,979, filed on Sep. 2, 2021.

(51) Int. Cl.
*C07D 403/14* (2006.01)
*A61K 31/497* (2006.01)

(52) U.S. Cl.
CPC .......... *C07D 403/14* (2013.01); *A61K 31/497* (2013.01)

(58) Field of Classification Search
CPC .................................................... C07D 403/14
See application file for complete search history.

(56) References Cited

U.S. PATENT DOCUMENTS

2016/0228373 A1   8/2016   Duarte et al.

FOREIGN PATENT DOCUMENTS

| JP | 2016-536134 A | 11/2016 |
|---|---|---|
| WO | 2007/007041 A1 | 1/2007 |
| WO | 2011/135355 A1 | 11/2011 |
| WO | 2012/007758 A2 | 1/2012 |
| WO | 2010/092386 A1 | 8/2012 |
| WO | 2021/186151 A1 | 9/2021 |

OTHER PUBLICATIONS

International Search Report dated May 12, 2023 issued in PCT Application No. PCT/IB2022/000775.

*Primary Examiner* — Brian E McDowell
(74) *Attorney, Agent, or Firm* — RAPHAEL BELLUM PLLC

(57) ABSTRACT

Cocrystals of a benzamide compound, specifically 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide, therapeutic uses of the benzamide cocrystals and pharmaceutical compositions containing them are disclosed. For purposes of this disclosure and for ease of understanding, "benzamide" or "benzamide compound" as well as "AZD1656" refer to 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide. The benzamide cocrystals of the invention include a 1:1 benzamide fumaric acid (Cocrystal 1), a 1:1 benzamide maleic acid (Cocrystal 2), a 1:1 benzamide malonic acid (Cocrystal 3), a 1:1 benzamide L-tartaric acid hydrate (Cocrystal 4), and a 1:1 benzamide gentisic acid (Cocrystal 5), which includes a 1:1 benzamide gentisic acid form 1 (Cocrystal 5A), a 1:1 benzamide gentisic acid form 2 (Cocrystal 5B), a 1:1 benzamide gentisic acid form 3 (Cocrystal 5C), and a 1:1 benzamide gentisic acid form 4 (Cocrystal 5D).

14 Claims, 32 Drawing Sheets

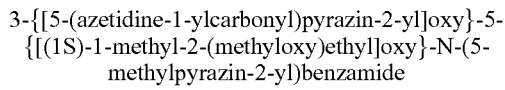

THERAPEUTIC COCRYSTALS OF 3-{[5-(AZETIDINE-1-YLCARBONYL)PYRAZIN-2-YL]OXY}-5-{[(1S)-1-METHYL-2-(METHYLOXY)ETHYL]OXY)-N-(5-METHYLPYRAZIN-2-YL)BENZAMIDE

CROSS-REFERENCE TO RELATED APPLICATION

This application claims priority to U.S. Provisional Application No. 63/239,979, filed on Sep. 2, 2021, the disclosure of which is incorporated by reference.

FIELD OF THE INVENTION

This invention relates to cocrystals of a benzamide compound, specifically 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide, therapeutic uses of the benzamide cocrystals and pharmaceutical compositions containing them. The benzamide cocrystals of the invention include a 1:1 benzamide fumaric acid (Cocrystal 1), a 1:1 benzamide maleic acid (Cocrystal 2), a 1:1 benzamide malonic acid (Cocrystal 3), a 1:1 benzamide L-tartaric acid hydrate (Cocrystal 4), and a 1:1 benzamide gentisic acid (Cocrystal 5), which includes a 1:1 benzamide gentisic acid form 1 (Cocrystal 5A), a 1:1 benzamide gentisic acid form 2 (Cocrystal 5B), a 1:1 benzamide gentisic acid form 3 (Cocrystal 5C), and a 1:1 benzamide gentisic acid form 4 (Cocrystal 5D).

BACKGROUND

The benzamide compound, 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide, illustrated below, and disclosed in WO 2007/007041, is an activator of glucokinase (GLK or GK) and as such is useful in the treatment or prevention of a disease or medical condition mediated through glucokinase. The benzamide compound, 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide is more commonly referred to as AZD1656. For purposes of this disclosure and for ease of understanding, "benzamide" or "benzamide compound" as well as "AZD1656" refer to 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide.

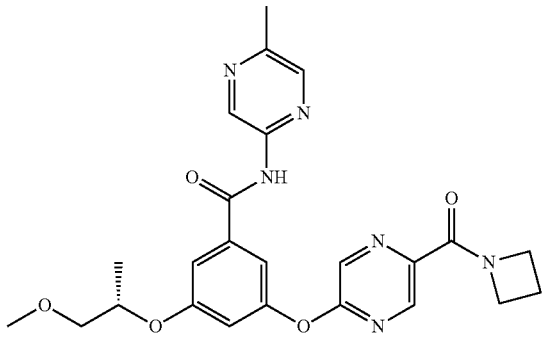 [SMILES: COC[C@H](C)Oc1cc(Oc2cnc(C(=O)N3CCC3)cn2)cc(C(=O)Nc2cnc(C)cn2)c1]

Benzamide Compound

3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide WO 2007/007041 discloses two polymorphic crystalline forms of the benzamide compound (Form 1 and Form 2) and a dihydrate crystalline form (Form 3). Three further polymorphic crystalline forms of the benzamide compound are disclosed in WO 2010/092386 (Form 4, Form 5 and Form 6). Form 6 was the form selected for drug product development and has been the form used in all clinical trials of the benzamide compound to date. It is known that different polymorphic forms of a drug substance can have different chemical and physical properties, including melting point, apparent solubility, dissolution rate, mechanical properties, vapour pressure, and density. These properties have a direct effect on the manufacture of a drug product as well as its stability, dissolution, and bioavailability. Thus, polymorphism can affect the quality, safety, and efficacy of a drug product. The ability of a drug substance to exist in multiple polymorphic forms can at times be problematic and may lead to the transition of polymorphic forms during drug manufacture or even within the drug product itself during storage.

WO 2012/007758 discloses processes for reducing the particle size of 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide to ensure satisfactory dissolution behaviour of the drug. During micronisation of certain compounds that have strong inherent cohesion and/or significant adhesion to stainless steel or titanium nitride it has been found that the material builds up on the surfaces of the milling equipment. See WO 2012/007758, p. 1, I. 20-22. This results in a loss of material, a non-homogenous product, diminished speed and efficiency of the process, increased processing times and costs, and in severe cases prevention from being carried out on a commercial scale. Id. at p. 1, I. 22-26. WO 2012/007758 solves this problem by milling 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide with one or more co-milling excipients, such as lactose or mannitol, optionally in the presence of a surfactant. Id. at p. 2, I. 13-20. Needing a co-milling excipient may result in the current tablet formulation having a limit to the amount of 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide in a single tablet. This may result in a high pill burden or an unsuitable formulation for delivery methods such as intravenous, inhalation, etc. Therefore, there is still a need for new solid forms as every unique solid form has different cohesive/adhesive properties along with potentially having a sufficient dissolution rate where particle size reduction is not needed.

It may be possible to achieve more desirable properties of a particular active pharmaceutical ingredient (API) by forming a cocrystal of the API. A cocrystal of an API is a distinct crystalline chemical composition of the API and coformer(s) and generally possesses distinct crystallographic and spectroscopic properties when compared to those of the API and coformer(s) individually. Crystallographic and spectroscopic properties of crystalline forms are typically measured by X-ray powder diffraction (XRPD) and single crystal X-ray crystallography, among other techniques. Cocrystals often also exhibit distinct thermal behavior. Thermal behavior is measured in the laboratory by such techniques as capillary melting point, thermogravimetric analysis (TGA) and differential scanning calorimetry (DSC). Cocrystals often possess more favorable solid state, physical, chemical, pharmaceutical and/or pharmacological properties or be easier to process than known forms or formulations of the API. For example, a cocrystal may have different dissolution and/or solubility properties than the API and can therefore be more effective in therapeutic delivery. Formation of a cocrystal can be used as a way to avoid polymorph formation of the drug. New pharmaceutical compositions comprising a cocrystal of a given API may therefore have different or superior properties as compared to its existing drug formulations.

Unlike salts, which possess a neutral net charge, but which are comprised of charge-balanced components, cocrystals are comprised of neutral species. Thus, unlike a salt, one cannot determine the stoichiometry of a cocrystal based on charge balance. Indeed, one can often obtain cocrystals having stoichiometric ratios of drug to coformer of greater than or less than 1:1. The stoichiometric ratio of an API to coformer is a generally unpredictable feature of a cocrystal.

Without limiting the disclosed invention to any particular definition because others may define the term differently, the term 'cocrystal' may be thought of as a multi-component crystal composed of neutral molecules. These multi-component assemblies are continuing to excite and find usefulness, particularly within the pharmaceutical field, for their ability to alter physicochemical properties. More specifically, cocrystals have been reported to alter melting point, aqueous solubility and/or dissolution rates, increase stability and improve bioavailability of active pharmaceutical ingredients.

SUMMARY OF THE INVENTION

The invention relates to novel cocrystals of a benzamide compound, specifically 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide. Here, "benzamide" or "benzamide compound" refer to 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide.

In particular, the benzamide cocrystals of the invention include a 1:1 benzamide fumaric acid (Cocrystal 1), a 1:1 benzamide maleic acid (Cocrystal 2), a 1:1 benzamide malonic acid (Cocrystal 3), a 1:1 benzamide L-tartaric acid hydrate (Cocrystal 4), and a 1:1 benzamide gentisic acid (Cocrystal 5), which includes a 1:1 benzamide gentisic acid form 1 (Cocrystal 5A), a 1:1 benzamide gentisic acid form 2 (Cocrystal 5B), a 1:1 benzamide gentisic acid form 3 (Cocrystal 5C), and a 1:1 benzamide gentisic acid form 4 (Cocrystal 5D).

The invention also relates to pharmaceutical compositions containing a benzamide cocrystal of the invention and a pharmaceutically acceptable carrier. The benzamide cocrystals of the invention may be used in the same way as the benzamide compound. The benzamide compound is an activator of glucokinase (GLK or GK) and as such is useful in the treatment or prevention of a disease or medical condition mediated through glucokinase. The benzamide cocrystals of the invention as such may be useful for the treatment of the diseases, disorders and conditions associated with such properties.

DETAILED DESCRIPTION

Figure 1:
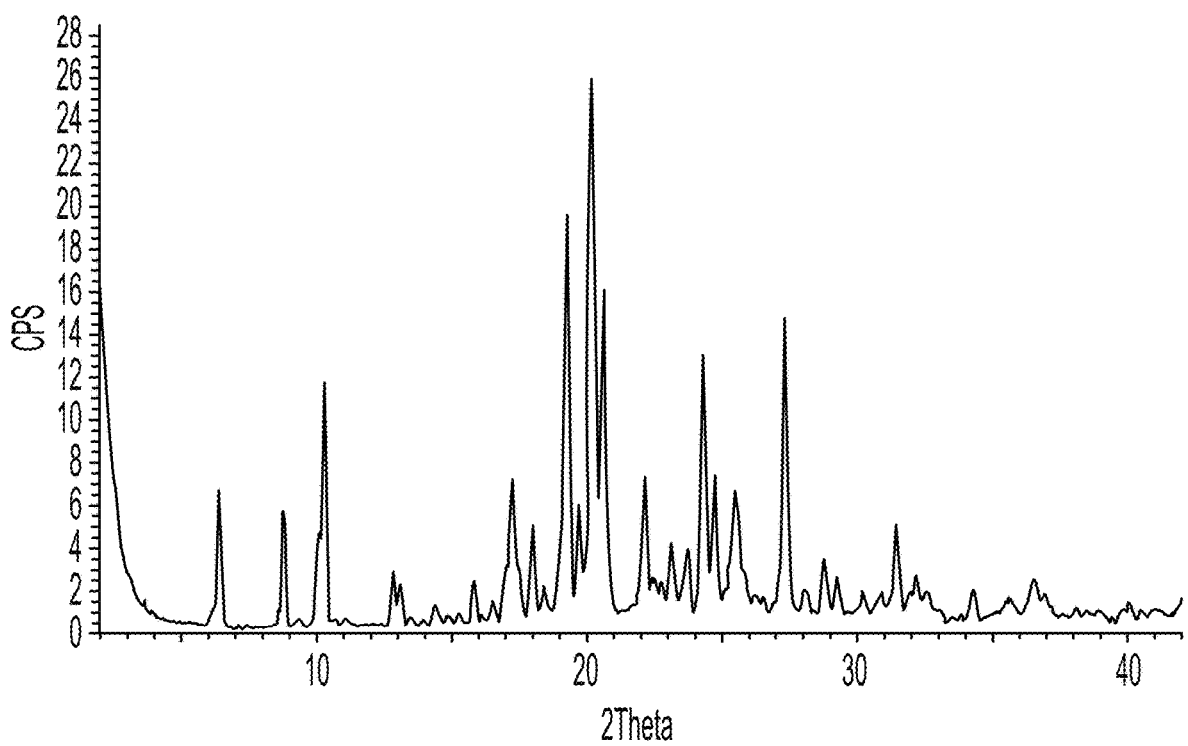
FIG. 1 shows an XRPD diagram of the 1:1 benzamide fumaric acid cocrystal (Cocrystal 1).

The invention relates to novel cocrystals of a benzamide compound, specifically 3-{[5-(azetidine-1-ylcarbonyl)

pyrazin-2-yl]oxy}-5-{[(1S)-1-methyl-2-(methyloxy)ethyl]oxy}-N-(5-methylpyrazin-2-yl)benzamide. As mentioned, "benzamide" or "benzamide compound" as well as "AZD1656" refer to 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide.

In particular, the benzamide cocrystals of the invention include a 1:1 benzamide fumaric acid (Cocrystal 1), a 1:1 benzamide maleic acid (Cocrystal 2), a 1:1 benzamide malonic acid (Cocrystal 3), a 1:1 benzamide L-tartaric acid hydrate (Cocrystal 4), and a 1:1 benzamide gentisic acid (Cocrystal 5), which includes a 1:1 benzamide gentisic acid form 1 (Cocrystal 5A), a 1:1 benzamide gentisic acid form 2 (Cocrystal 5B), a 1:1 benzamide gentisic acid form 3 (Cocrystal 5C), and a 1:1 benzamide gentisic acid form 4 (Cocrystal 5D).

The benzamide cocrystals of the invention, their preparation and their characterization are described in the examples below and shown in the figures. The invention relates to pharmaceutical compositions containing a therapeutically effective amount of a benzamide cocrystal of the invention and a pharmaceutically acceptable carrier. The invention also relates to methods of treatment for the diseases, disorders and conditions described herein and the use of a therapeutically effective amount of a benzamide cocrystal of the invention, or a pharmaceutical composition containing it, for that treatment. The invention further provides the use of a benzamide cocrystal of the invention in the manufacture of a medicament for use in the treatment of the diseases, disorders and conditions described herein.

Therapeutic Uses of Benzamide Cocrystals of the Invention

As discussed above, the benzamide compound, AZD1656, is known in the art to be useful in the treatment or prevention of various diseases, disorders and conditions that are mediated through glucokinase (GSK or GL). The benzamide cocrystals of the invention, a 1:1 benzamide fumaric acid (Cocrystal 1), a 1:1 benzamide maleic acid (Cocrystal 2), a 1:1 benzamide malonic acid (Cocrystal 3), a 1:1 benzamide L-tartaric acid hydrate (Cocrystal 4), and a 1:1 benzamide gentisic acid (Cocrystal 5), which includes a 1:1 benzamide gentisic acid form 1 (Cocrystal 5A), a 1:1 benzamide gentisic acid form 2 (Cocrystal 5B), a 1:1 benzamide gentisic acid form 3 (Cocrystal 5C), and a 1:1 benzamide gentisic acid form 4 (Cocrystal 5D), and pharmaceutical compositions containing them may then also be used to treat such diseases, disorders and conditions.

Accordingly, the invention relates to the method of treating a disease, disorder, or condition mediated through glucokinase (GSK or GL) comprising the step of administering to a patient in need thereof a therapeutically effective amount of a benzamide cocrystal of the invention or of administering to a patient in need thereof a therapeutic composition containing a benzamide cocrystal of the invention.

In one embodiment of the invention, the disease, disorder, or condition mediated through glucokinase (GSK or GL) is selected from Type 1 Diabetes, Type 2 Diabetes, dyslipidemia, obesity, insulin resistance, metabolic syndrome X, and impaired glucose tolerance. The invention relates to a method of treating Type 1 Diabetes, Type 2 Diabetes, dyslipidemia, obesity, insulin resistance, metabolic syndrome X, or impaired glucose tolerance by administering to a patient in need thereof a therapeutically effective amount of a benzamide cocrystal of the invention or a therapeutic composition containing a benzamide cocrystal of the invention.

In one embodiment of the invention, the disease, disorder, or condition mediated through glucokinase (GSK or GL) where an inappropriate T-cell mediated response is involved is selected from respiratory viral infections, organ transplant rejection, and T-cell mediated auto-immune conditions. In a further embodiment of the invention, the disease, disorder, or condition mediated through glucokinase (GSK or GL) where an inappropriate T-cell mediated response is involved is selected from Renal transplant rejection, uveitis, premature labor, Hashimoto's thyroiditis, psoriasis, arteriosclerosis, autoimmune Addison's disease, autoimmune hepatitis, autoimmune myocarditis, autoimmune pancreatitis, autoimmune retinopathy, coeliac disease, Crohn's disease, discoid lupus, idiopathic pulmonary fibrosis, irritable bowel syndrome, lupus nephritis, autoimmune Meniere's disease, multiple sclerosis, psoriatic arthritis, rheumatoid arthritis, sarcoidosis, systemic lupus, ulcerative colitis, and thyroiditis. The invention relates to a method of treating respiratory viral infections, organ transplant rejection, or T-cell mediated auto-immune conditions by administering to a patient in need thereof a therapeutically effective amount of a benzamide cocrystal of the invention or a therapeutic composition containing a benzamide cocrystal of the invention. The invention further relates to a method of treating Renal transplant rejection, uveitis, premature labor, Hashimoto's thyroiditis, psoriasis, arteriosclerosis, autoimmune Addison's disease, autoimmune hepatitis, autoimmune myocarditis, autoimmune pancreatitis, autoimmune retinopathy, coeliac disease, Crohn's disease, discoid lupus, idiopathic pulmonary fibrosis, irritable bowel syndrome, lupus nephritis, autoimmune Meniere's disease, multiple sclerosis, psoriatic arthritis, rheumatoid arthritis, sarcoidosis, systemic lupus, ulcerative colitis, and thyroiditis by administering to a patient in need thereof a therapeutically effective amount of a benzamide cocrystal of the invention or a therapeutic composition containing a benzamide cocrystal of the invention. A therapeutically effective amount of a benzamide cocrystal of the invention or a therapeutic composition containing a benzamide cocrystal of the invention may control innate and adaptive immune responses by enhancing the migration of regulatory T-cells (Tregs) to inflammation sites, thereby reducing inflammation and helping restore immune homeostasis.

The term "treatment" or "treating" means any treatment of a disease, disorder or condition in a mammal, including: preventing or protecting against the disease, disorder or condition, that is, causing the clinical symptoms not to develop; inhibiting the disease, disorder or condition, that is, arresting or suppressing the development of clinical symptoms; and/or relieving the disease, disorder or condition (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the disease, disorder, or condition. The term "protection" is meant to include "prophylaxis."

Another aspect of the invention relates to the use of a benzamide cocrystal of the invention in the treatment of diseases, disorders and conditions discussed above. Accordingly, the invention further relates to the manufacture of a medicament for use in the treatment of such diseases, disorders, and conditions.

Pharmaceutical Compositions Containing Benzamide Cocrystals of the Invention

The invention relates to pharmaceutical compositions comprising, consisting essentially, or consisting of a therapeutically effective amount of a benzamide cocrystal of the invention and a pharmaceutically acceptable carrier (also known as a pharmaceutically acceptable excipient). As mentioned above, these pharmaceutical compositions are therapeutically useful to treat or prevent disorders mediated through glucokinase (GSK or GL), such as those discussed above. A pharmaceutical composition of the invention may be a solid dosage form, or a solution made with a benzamide cocrystal of the invention.

A pharmaceutical composition of the invention may be in any pharmaceutical form which contains a benzamide cocrystal of the invention. The pharmaceutical composition may be, for example, a tablet, a capsule, an oral solution, an injectable composition, a topical composition, an inhalable composition, or a transdermal composition. Liquid pharmaceutical compositions may be prepared using a benzamide cocrystal of the invention and represent a particular embodiment of the invention. For a liquid pharmaceutical composition, the benzamide cocrystal of the invention may be dissolved in a solvent, e.g., water, at the time and point of care.

The pharmaceutical compositions generally contain, for example, about 0.1% to about 99.9% by weight of a benzamide cocrystal of the invention, for example, about 0.5% to about 99.5% by weight of a benzamide cocrystal of the invention and, for example, 99.5% to 0.5% by weight of at least one suitable pharmaceutical excipient or solvent. In one embodiment, the composition may be between about 5% and about 75% by weight of a benzamide cocrystal of the invention with the rest being at least one suitable pharmaceutical excipient, solvent or at least one other adjuvant, as discussed below.

A "therapeutically effective amount of a benzamide cocrystal of the invention" is that which correlates to a therapeutic effect and may for example, be about 25 mg-about 300 mg, about 50 mg-about 250 mg, about 75 mg-about 225 mg, or preferably about 100 mg-about 200 mg. The actual amount required for treatment of any particular disease, disorder or condition for any particular patient may depend upon a variety of factors including, for example, the particular disease, disorder or condition being treated; the disease state being treated and its severity; the specific pharmaceutical composition employed; the age, body weight, general health, sex and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used. For a pharmaceutical composition of the invention, that is one containing a benzamide cocrystal of the invention, a carrier should be chosen that maintains the crystalline form. In other words, the carrier should not substantially alter the benzamide cocrystal of the invention. Nor should the carrier be otherwise incompatible with a benzamide cocrystal of the invention used, such as by producing any undesirable biological effect or otherwise interacting in a deleterious manner with any other component(s) of the pharmaceutical composition.

The pharmaceutical compositions of the invention may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, a benzamide cocrystal of the invention may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others, as is known in the pharmaceutical art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Compositions for rectal administrations are, for example, suppositories that may be prepared by mixing a benzamide cocrystal of the invention with, for example, suitable non-irritating excipients or carriers such as cocoa butter, polyethylene glycol or a suppository wax, which may be solid at ordinary temperatures but may be liquid at body temperature and, therefore, melt while in a suitable body cavity and release the active component therein.

Compositions suitable for topical administration include liquid or semi-liquid preparations such as liniments, lotions, gels, applicants, oil-in-water or water-in-oil emulsions such as creams, ointments, pastes or foams; or solutions or suspensions such as drops, as is known in the art. Compositions of the invention may be intended for topical administration, in which case the carrier may suitably comprise a solution, emulsion, ointment or gel base. The carrier or base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

In addition to the topical method of administration described above, there are various methods of administering the active benzamide cocrystal of the invention topically to the lung. One such means could involve a dry powder inhaler formulation of respirable particles comprised of a benzamide cocrystal of the invention, which the patient being treated inhales. It is common for a dry powder formulation to include carrier particles, to which particles of a benzamide cocrystal of the invention can adhere to. The carrier particles may be of any acceptable pharmacologically inert material or combination of materials. For example, the carrier particles may be composed of one or more materials selected from sugar alcohols; polyols, for example sorbitol, mannitol or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose.

In addition to the topical method of administration described above, there are various methods of administering the active benzamide cocrystals of the invention systemically by such methods. One such means would involve an aerosol suspension of respirable particles comprised of a benzamide cocrystal of the invention, which the patient being treated inhales. A benzamide cocrystal of the invention would be absorbed into the bloodstream via the lungs in a pharmaceutically effective amount. The respirable particles can be liquid or solid, with a particle size sufficiently small to pass through the mouth and larynx upon inhalation.

Because the crystalline form of a benzamide cocrystal of the invention may be maintained during preparation, solid dosage forms are one embodiment of the pharmaceutical composition of the invention. Dosage forms for oral administration, which includes capsules, tablets, pills, powders, granules, and suspensions may be used. Dosage forms for pulmonary administration, which includes metered dose inhaler, dry powder inhaler or aerosol formulations may be used. In such solid dosage forms, the active compound may be mixed with at least one inert, pharmaceutically acceptable excipient (also known as a pharmaceutically acceptable carrier).

A benzamide cocrystal of the invention may also be used to formulate liquid or injectable pharmaceutical compositions. Administration of a benzamide cocrystal of the invention in pure form or in an appropriate pharmaceutical composition may be carried out via any of the accepted modes of administration or agents for serving similar utilities. Thus, administration may be, for example, orally, buccally, nasally, pulmonary, parenterally (intravenous, intramuscular, or subcutaneous), topically, transdermally, intravaginally, intravesically, intrasystemically, ophthalmically or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

The invention also relates to a method of preparing a liquid pharmaceutical composition comprising the step of dissolving a benzamide cocrystal of the invention in a pharmaceutically acceptable solvent and to liquid pharmaceutical compositions prepared according to that method. As discussed above, liquid pharmaceutical compositions of the invention may be administered orally, parenterally (including by inhalation), and intravenously.

EXAMPLES

The following analytical methods were used to characterise the benzamide cocrystals of the invention:

X-Ray Powder Diffraction (XRPD) Characterisation: XRPD diffractograms were collected on a Bruker D8 diffractometer using Cu Kα radiation (40 kV, 40 mA) and a 6-26 goniometer fitted with a Ge monochromator. The incident beam passes through a 2.0 mm divergence slit followed by a 0.2 mm antiscatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively. Samples were run under ambient conditions over an angular range of 2° to 42° 2θ (using a step size of 0.05° 2θ and a step time of 0.5 seconds) as flat plate specimens using powder as received. The sample was prepared on a polished, zero-background (510) silicon wafer by gently pressing onto the flat surface or packed into a cut cavity. The sample was rotated in its own plane. Small D8 disc recess holders were used to prepare sample.

Single Crystal X-Ray Diffraction (SCXRD): Data were collected at room temperature on an Oxford Diffraction SuperNova Dual source, Cu at zero, Atlas CCD Diffractometer. Structures were solved using the Bruker SHELXTL program and refined with the SHELXTL program as part of the Bruker SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Thermal Analysis—Differential Scanning Calorimetry (DSC): DSC data were collected on a PerkinElmer Pyris 4000 DSC equipped with a 45 position sample holder. The instrument was verified for energy and temperature calibration using certified indium. A predefined amount of the sample, 0.5-3.0 mg, was placed in a pin holed aluminium pan and heated at 20° C.·min$^{-1}$ from 30 to 350° C. A purge of dry nitrogen at 60 ml·min$^{-1}$ was maintained over the sample. The instrument control, data acquisition and analysis were performed with Pyris Software v9.0.1.0203.

Thermo-Gravimetric Analysis (TGA): TGA data were collected on a TA Instruments Q500 TGA, equipped with a 16 position autosampler. Typically, 5-10 mg of each sample was loaded onto a pre-tared aluminium DSC pan and heated at 10° C./min from ambient temperature to 350° C. A nitrogen purge at 60 ml/min was maintained over the sample. The instrument control software was Advantage for Q Series and Thermal Advantage and the data were analysed using Universal Analysis or TRIOS.

Solution Proton Nuclear Magnetic Resonance (NMR): $^1$H NMR spectra were collected using a Bruker 400 MHz instrument equipped with an autosampler and controlled by an Avance NEO nanobay console. The samples were dissolved in d6-DMSO for analysis. The data was acquired using ICONNMR configuration within Topspin software.

In the examples below, the benzamide compound, 3-{[5-(azetidine-1-ylcarbonyl)pyrazin-2-yl]oxy}-5-{[(1S)-1-methyl-2-(methyloxy)ethyl]oxy}-N-(5-methylpyrazin-2-yl)benzamide, may be referred to as AZD1656.

Example 1: 1:1 Benzamide Fumaric Acid Cocrystal (Cocrystal 1)

Preparation of Cocrystal 1

The batch of Cocrystal 1 used for characterisation was prepared as follows:

Procedure 1:

AZD1656 (456 mg, 0.95 mmol) and fumaric acid (111 mg, 0.95 mmol) were milled with nitromethane (3 drops) for 3×20 minutes at 30 Hz in a Retsch ball mill. The product was dried in-vacuo at 40° C. overnight.

Procedure 2:

AZD1656 (139 mg, 0.29 mmol) and fumaric acid (33 mg, 0.28 mmol) were placed in a glass vial and nitromethane (2 ml) was added. The resulting slurry was placed in a shaker and matured for 24 hours (room temperature to 50° C. on an 8-hour cycle, heating to 50° C. for 4 hours and then cooling to room temperature for 4 hours). The product was then filtered under vacuum and dried in-vacuo at 40° C. overnight.

XRPD Characterisation of Cocrystal 1

The experimental XRPD pattern of Cocrystal 1 prepared by procedure 1 is shown in FIG. 1. Table 1 lists the angles, ° 2θ±0.2° 2θ, and d-spacing of the peaks identified in the experimental XRPD pattern of FIG. 1. The entire list of peaks, or a subset thereof, may be sufficient to characterize the cocrystal, as well as by an XRPD pattern substantially similar to FIG. 1. For example, the cocrystal may be characterized by at least two, at least three, at least four or all of the peaks selected from the peaks at 6.4, 8.7, 14.4, 15.9, 22.2 and 27.3° 2θ±0.2° 2θ.

TABLE 1

| Angle °2θ ± 0.2 °2θ | d value Angstrom | Intensity % |
|---|---|---|
| 6.4 | 13.73 | 21% |
| 8.7 | 10.10 | 19% |
| 10.1 | 8.76 | 16% |
| 10.3 | 8.60 | 40% |
| 12.8 | 6.88 | 9% |
| 13.1 | 6.77 | 7% |
| 14.4 | 6.15 | 4% |
| 15.9 | 5.59 | 7% |
| 17.2 | 5.14 | 25% |
| 17.5 | 5.06 | 7% |
| 18.0 | 4.93 | 16% |
| 18.4 | 4.81 | 5% |
| 19.3 | 4.60 | 73% |
| 19.7 | 4.50 | 19% |
| 20.2 | 4.39 | 100% |
| 20.6 | 4.30 | 59% |
| 22.2 | 4.01 | 23% |
| 22.7 | 3.91 | 4% |
| 23.1 | 3.84 | 12% |
| 23.7 | 3.75 | 11% |
| 24.3 | 3.66 | 47% |
| 24.8 | 3.59 | 24% |
| 25.5 | 3.49 | 19% |
| 27.3 | 3.26 | 56% |
| 28.0 | 3.18 | 5% |
| 28.8 | 3.10 | 10% |
| 30.2 | 2.96 | 4% |
| 30.9 | 2.89 | 4% |
| 31.5 | 2.84 | 16% |
| 32.2 | 2.78 | 6% |
| 34.3 | 2.61 | 6% |
| 36.6 | 2.46 | 7% |

SCXRD Characterisation of Cocrystal 1

The single crystal used for single crystal structure determination was prepared as follows: approximately 5 mg (estimated by eye) of Cocrystal 1 was placed in a 2 ml glass vial and 500 μL of nitromethane was added. The solution was allowed to evaporate slowly at room temperature enabling crystal formation. A suitable crystal was selected for SCXRD characterisation.

Figure 2:
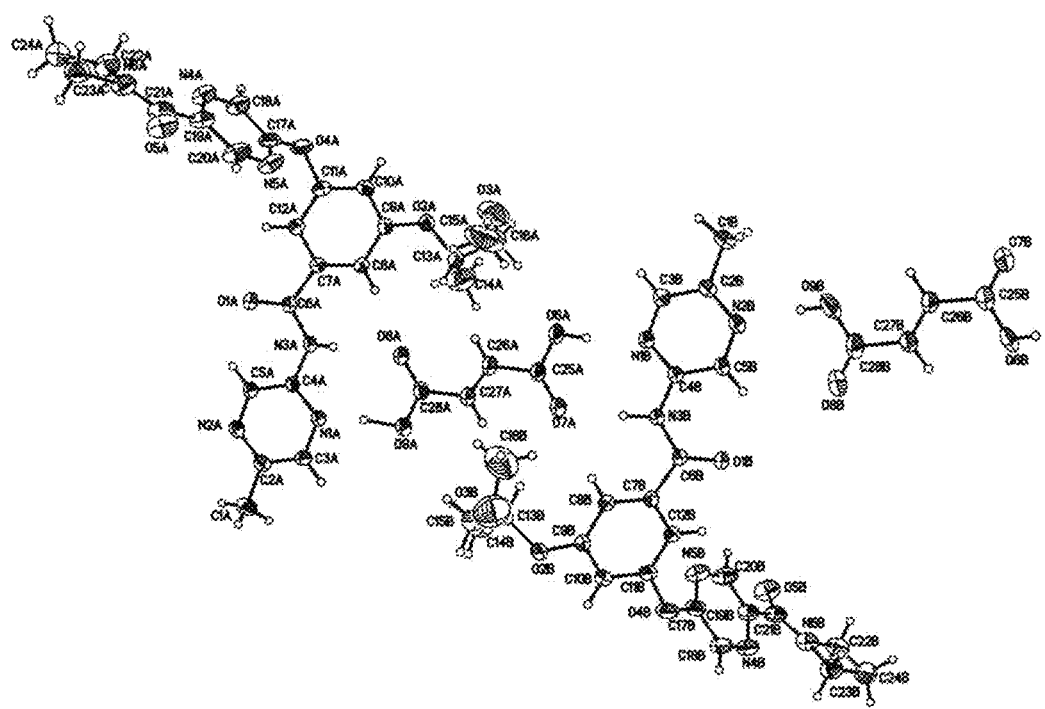
FIG. 2 shows an ORTEP drawing of the 1:1 benzamide fumaric acid cocrystal (Cocrystal 1) at 292 K.
Figure 3:
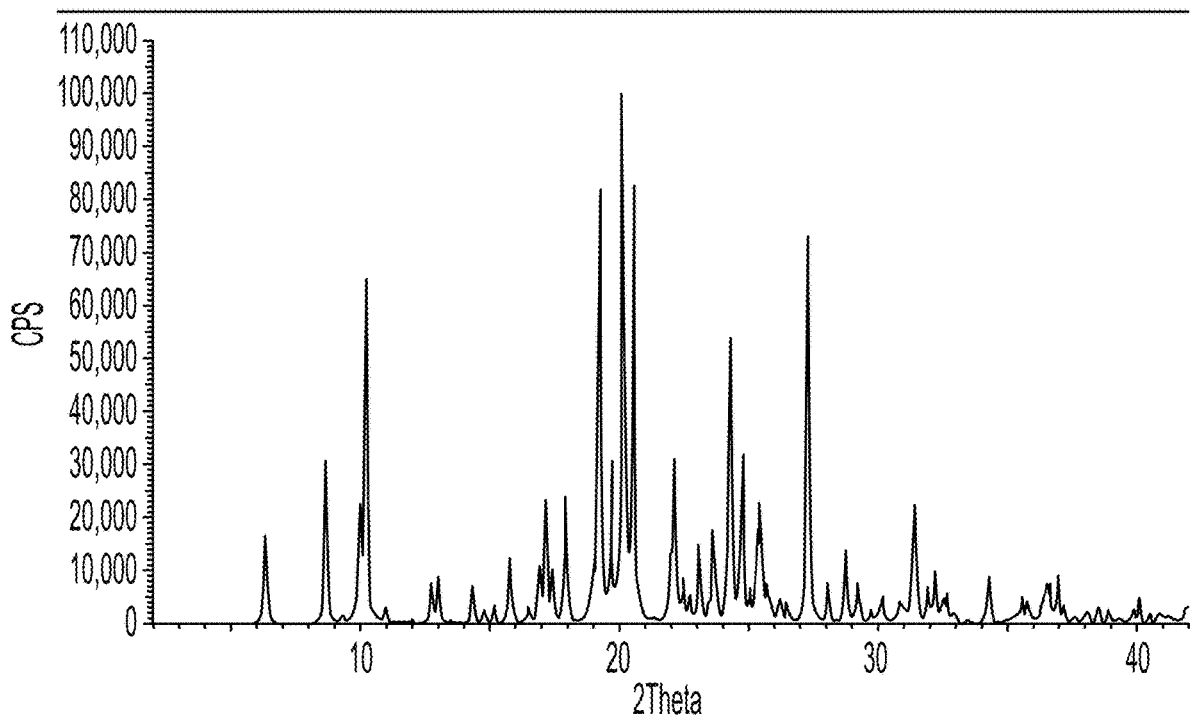
FIG. 3 shows a calculated XRPD pattern for the 1:1 benzamide fumaric acid cocrystal (Cocrystal 1) at 292 K.

The single crystal data and structure refinement parameters for the structure measured at room temperature are reported in Table 2, below. An ORTEP diagram of Cocrystal 1 at room temperature showing the numbering system employed is shown in FIG. 2. Anisotropic atomic displacement ellipsoids for the non-hydrogen atoms are shown at the 30% probability level and hydrogen atoms are displayed as spheres of arbitrary radius. The calculated XRPD pattern based on the single crystal data and structure for Cocrystal 1 at room temperature is shown in FIG. 3. It can be seen that there are small intensity differences between FIG. 1 and FIG. 3 owing to preferred orientation effects present in the experimental pattern.

TABLE 2

| | |
|---|---|
| Molecular formula | $C_{28}H_{30}N_6O_9$ |
| Molecular weight | 594.58 |
| Crystal System | Triclinic |
| Space Group | P1 |
| Unit Cell Dimensions | a = 9.8435(3) Å |
| | b = 11.4054(3) Å |
| | c = 15.0743(6) Å |
| | α = 95.605(3)° |
| | β = 108.628(3)° |
| | γ = 113.219(3)° |

TABLE 2-continued

| | |
|---|---|
| Cell Volume | 1424.42(9) Å³ |
| Z | 2 |
| Temperature | 292(4) K |
| Radiation Wavelength/type | 1.54184 Å/Cu Kα |
| Goodness of fit | 1.023 |
| R factor | 0.0472 |
| Morphology | Colourless lath |

DSC of Cocrystal 1

Figure 4:
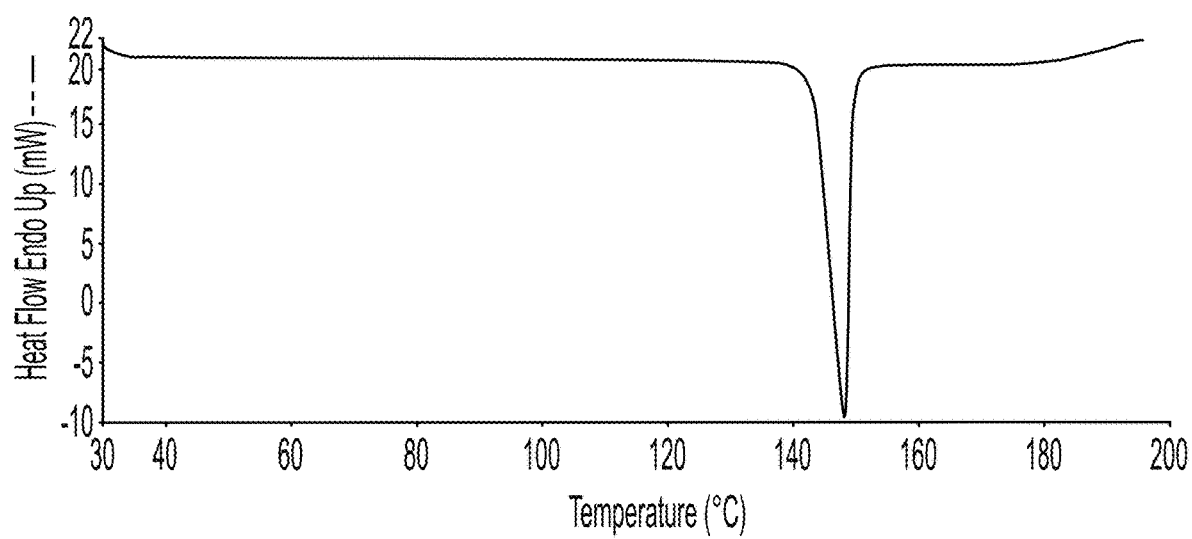
FIG. 4 shows a DSC trace for the 1:1 benzamide fumaric acid cocrystal (Cocrystal 1).

The differential scanning calorimetry (DSC) trace of Cocrystal 1, FIG. 4, shows a single endotherm with an onset temperature of 144.3° C. and a peak maximum of 148.4° C.

TGA of Cocrystal 1

Figure 5:
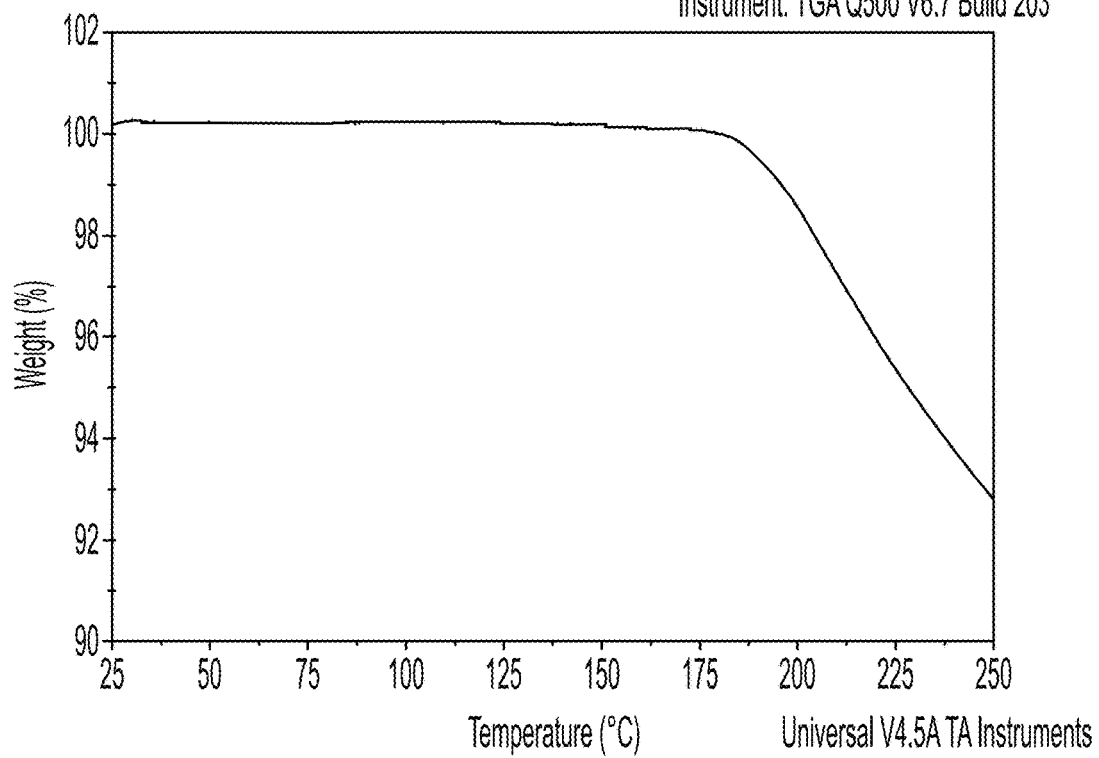
FIG. 5 shows a TGA trace for the 1:1 benzamide fumaric acid cocrystal (Cocrystal 1).

The thermal gravimetric analysis (TGA) trace of Cocrystal 1, FIG. 5, shows that there is no significant weight loss prior to 175° C. The TGA indicates that the cocrystal is anhydrous.

¹H NMR Spectrum of Cocrystal 1

Figure 6:
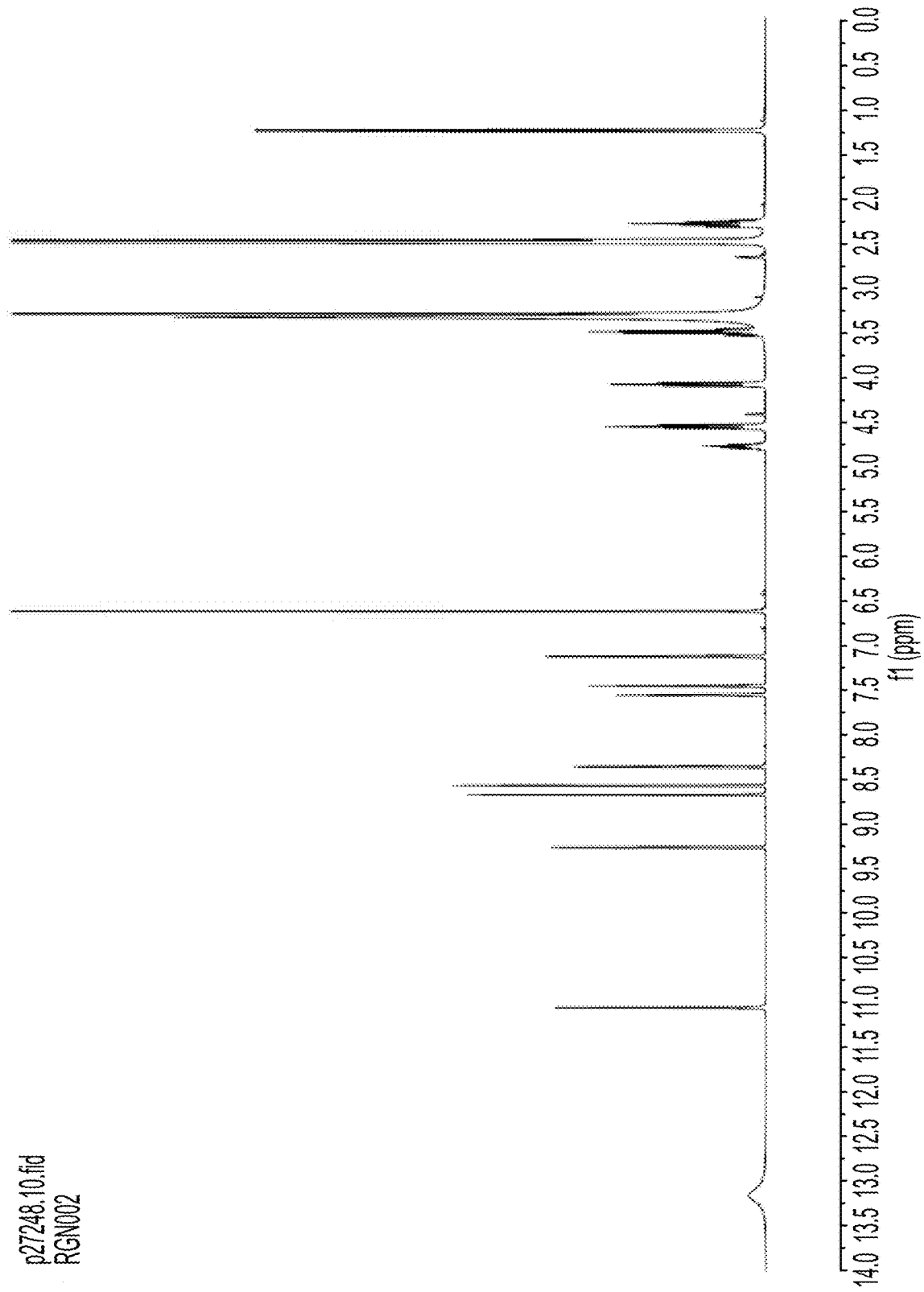
FIG. 6 shows the $^1$H NMR spectrum of 1:1 benzamide fumaric acid cocrystal (Cocrystal 1).

The ¹H NMR spectrum of Cocrystal 1, shown in FIG. 6, displays the following peaks: 1H NMR (400 MHz, DMSO): δ 1.24-1.26 (3H), 2.27-2.32 (2H), 2.48 (3H), 3.30 (3H), 3.46-3.55 (2H), 4.06-4.12 (2H), 4.52-4.59 (2H), 4.74-4.84 (1H), 6.62 (2H), 7.10-7.14 (1H), 7.45-7.49 (1H), 7.55-7.58 (1H), 8.34-8.39 (1H), 8.55-8.59 (1H), 8.66-8.70 (1H), 9.25-9.27 (1H), 11.05 (1H) and 13.0-13.5 (2H). The peak at 6.62 ppm in the ¹H NMR spectrum corresponds to two protons of fumaric acid. Comparison of the integration of this peak with that at 7.10-7.14, which corresponds to one proton of AZD1656, indicates that the cocrystal has as API:coformer stoichiometry of 1:1.

Polymorphism Study for Cocrystal 1

As AZD1656 is known to exist in six different crystalline forms an investigation was carried out to examine whether Cocrystal 1 could also exist in multiple polymorphic forms. Preparation methods 1 and 2 described above were carried out using 2-propanol, ethyl acetate, acetonitrile, methyl ethyl ketone and water. In all cases the same crystalline form of Cocrystal 1 was obtained indicating that this cocrystal exists as a single polymorphic form.

Example 2: 1:1 Benzamide Maleic Acid Cocrystal (Cocrystal 2)

Preparation of Cocrystal 2

The batch of Cocrystal 2 used for characterisation was prepared as follows:

Procedure 1:

AZD1656 (275 mg, 0.58 mmol) and maleic acid (66 mg, 0.58 mmol) were milled with ethanol (2 drops) for 3×20 minutes at 30 Hz in a Retsch ball mill. The product was dried in-vacuo at 40° C. overnight.

Procedure 2:

AZD1656 (164 mg, 0.34 mmol) and maleic acid (39 mg, 0.34 mmol) were placed in a glass vial and 2-propanol (1 ml) was added. The resulting slurry was placed in a shaker and matured for 24 hours (room temperature to 50° C. on an 8-hour cycle, heating to 50° C. for 4 hours and then cooling to room temperature for 4 hours). The product was then filtered under vacuum and dried in-vacuo at 40° C. overnight.

XRPD Characterisation of Cocrystal 2

Figure 7:
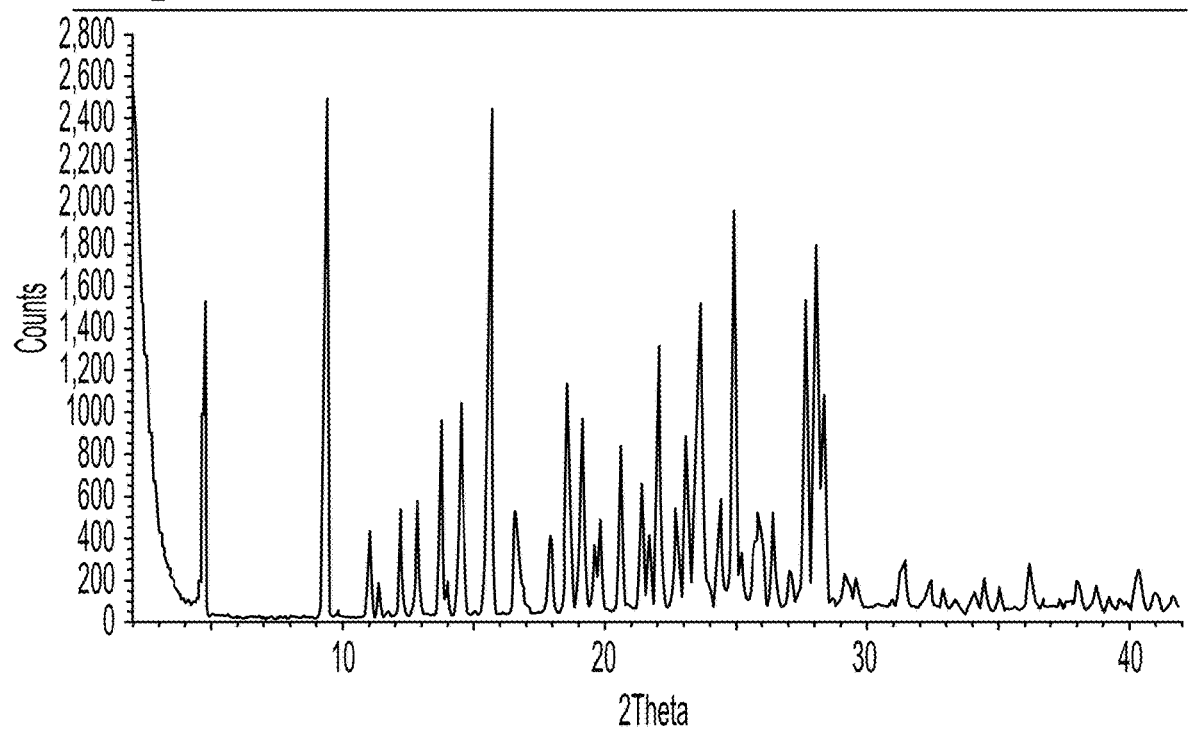
FIG. 7 shows an XRPD diagram of the 1:1 benzamide maleic acid cocrystal (Cocrystal 2).

The experimental XRPD pattern of Cocrystal 2 prepared by procedure 1 is shown in FIG. 7. Table 3 lists the angles, ° 2θ±0.2° 2θ, and d-spacing of the peaks identified in the experimental XRPD pattern of FIG. 7. The entire list of peaks, or a subset thereof, may be sufficient to characterize the cocrystal, as well as by an XRPD pattern substantially similar to FIG. 7. For example, the cocrystal may be characterized by at least two, at least three, at least four or all of the peaks selected from the peaks at 4.7, 9.3, 12.2, 12.8, 14.5 and 15.6° 2θ±0.2° 2θ.

TABLE 3

| Angle °2θ ± 0.2 °2θ | d value Angstrom | Intensity % |
|---|---|---|
| 4.7 | 18.9 | 45% |
| 9.3 | 9.48 | 84% |
| 11.0 | 8.04 | 23% |
| 11.4 | 7.78 | 9% |
| 12.2 | 7.26 | 18% |
| 12.8 | 6.89 | 19% |
| 13.8 | 6.39 | 28% |
| 14.0 | 6.32 | 8% |
| 14.5 | 6.11 | 39% |
| 15.6 | 5.67 | 87% |
| 16.6 | 5.33 | 17% |
| 17.9 | 4.95 | 14% |
| 18.6 | 4.77 | 43% |
| 19.2 | 4.63 | 35% |
| 19.6 | 4.53 | 18% |
| 19.9 | 4.46 | 24% |
| 20.6 | 4.31 | 31% |
| 21.4 | 4.15 | 38% |
| 21.7 | 4.09 | 18% |
| 22.1 | 4.02 | 48% |
| 22.7 | 3.91 | 18% |
| 23.1 | 3.84 | 32% |
| 23.7 | 3.75 | 56% |
| 24.4 | 3.65 | 20% |
| 25.0 | 3.57 | 100% |
| 25.2 | 3.53 | 14% |
| 25.9 | 3.44 | 17% |
| 26.5 | 3.36 | 17% |
| 27.1 | 3.29 | 6% |
| 27.7 | 3.22 | 57% |
| 28.1 | 3.17 | 98% |
| 28.4 | 3.14 | 56% |
| 31.5 | 2.84 | 8% |
| 32.5 | 2.76 | 5% |
| 33.0 | 2.72 | 4% |
| 34.5 | 2.59 | 6% |
| 35.1 | 2.56 | 4% |
| 36.3 | 2.47 | 9% |
| 38.1 | 2.36 | 8% |
| 38.8 | 2.32 | 5% |
| 40.4 | 2.23 | 7% |

SCXRD Characterisation of Cocrystal 2

The single crystal used for single crystal structure determination was prepared as follows: approximately 5 mg (estimated by eye) of Cocrystal 2 was placed in a 2 ml glass vial and 500 μL of ethyl acetate was added. The solution was allowed to evaporate slowly at room temperature enabling crystal formation. A suitable crystal was selected for SCXRD characterisation.

Figure 8:
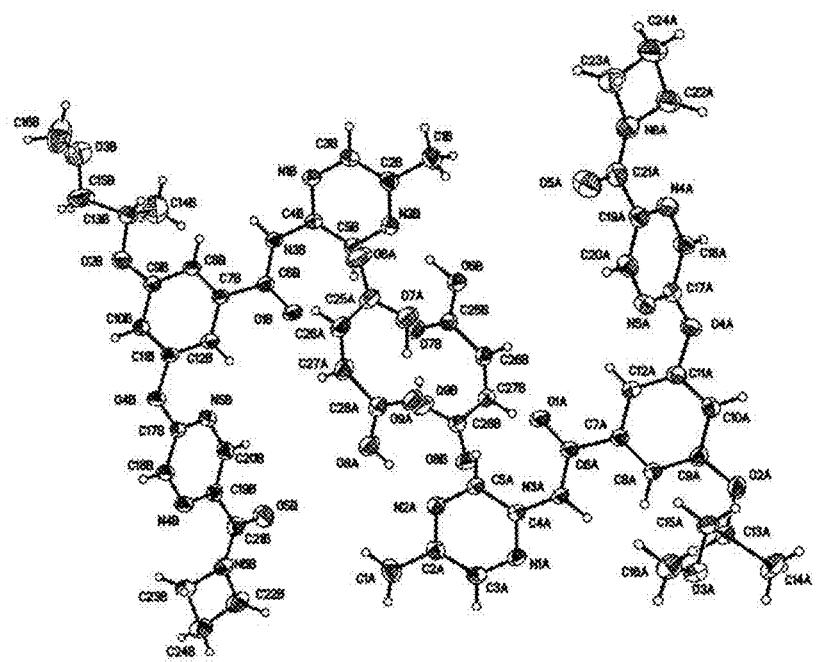
FIG. 8 shows an ORTEP drawing of the 1:1 benzamide maleic acid cocrystal (Cocrystal 2) at 292 K.
Figure 9:
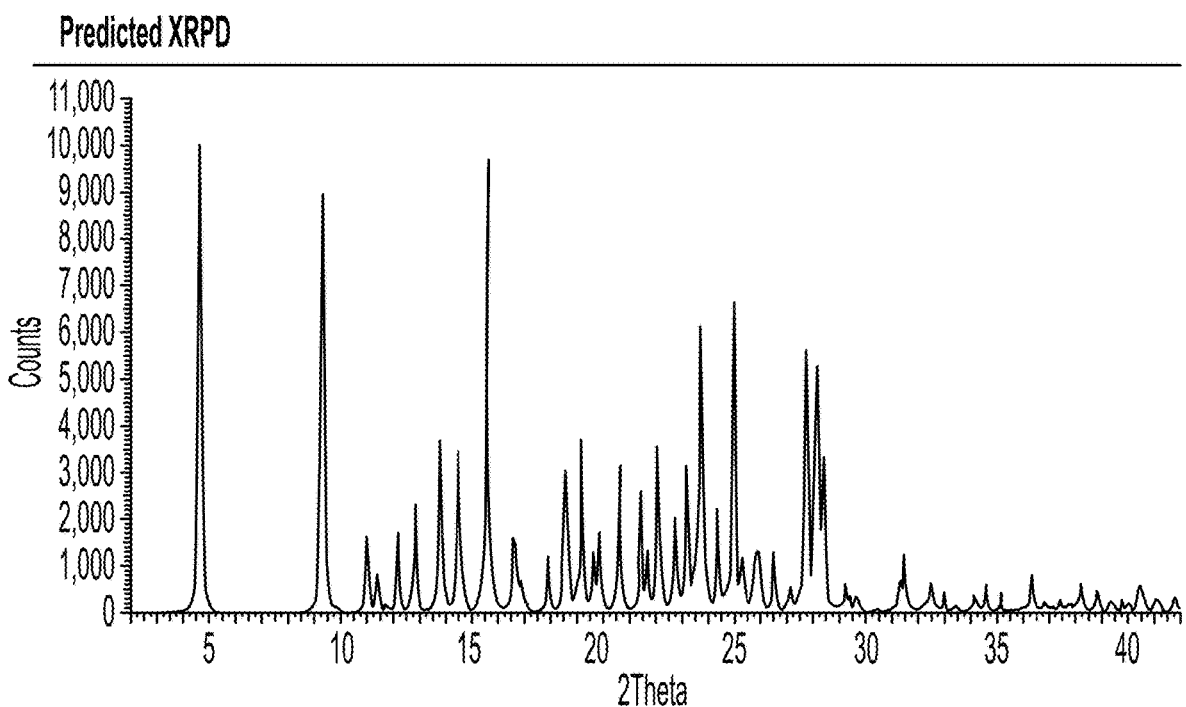
FIG. 9 shows a calculated XRPD pattern for the 1:1 benzamide maleic acid cocrystal (Cocrystal 2) at 292 K.

The single crystal data and structure refinement parameters for the structure measured at room temperature are reported in Table 4, below. An ORTEP diagram of Cocrystal 2 at room temperature showing the numbering system employed is shown in FIG. 8. Anisotropic atomic displacement ellipsoids for the non-hydrogen atoms are shown at the 30% probability level and hydrogen atoms are displayed as spheres of arbitrary radius. The calculated XRPD pattern based on the single crystal data and structure for Cocrystal 2 at room temperature is shown in FIG. 9. It can be seen that there are small intensity differences between FIG. 7 and FIG. 9 owing to preferred orientation effects present in the experimental pattern.

TABLE 4

| Molecular formula | $C_{28}H_{30}N_6O_9$ |
|---|---|
| Molecular weight | 594.58 |
| Crystal System | Triclinic |
| Space Group | P1 |
| Unit Cell Dimensions | a = 7.8811(2) Å |
| | b = 9.6568(2) Å |
| | c = 19.2761(4) Å |
| | α = 97.4767(17)° |
| | β = 97.5064(18)° |
| | ɣ = 96.242(2)° |
| Cell Volume | 1433.79(6) Å³ |
| Z | 2 |
| Temperature | 292(2) K |
| Radiation Wavelength/type | 1.54184 Å/Cu Kα |
| Goodness of fit | 1.042 |
| R factor | 0.0432 |
| Morphology | Colourless block |

DSC of Cocrystal 2

Figure 10:
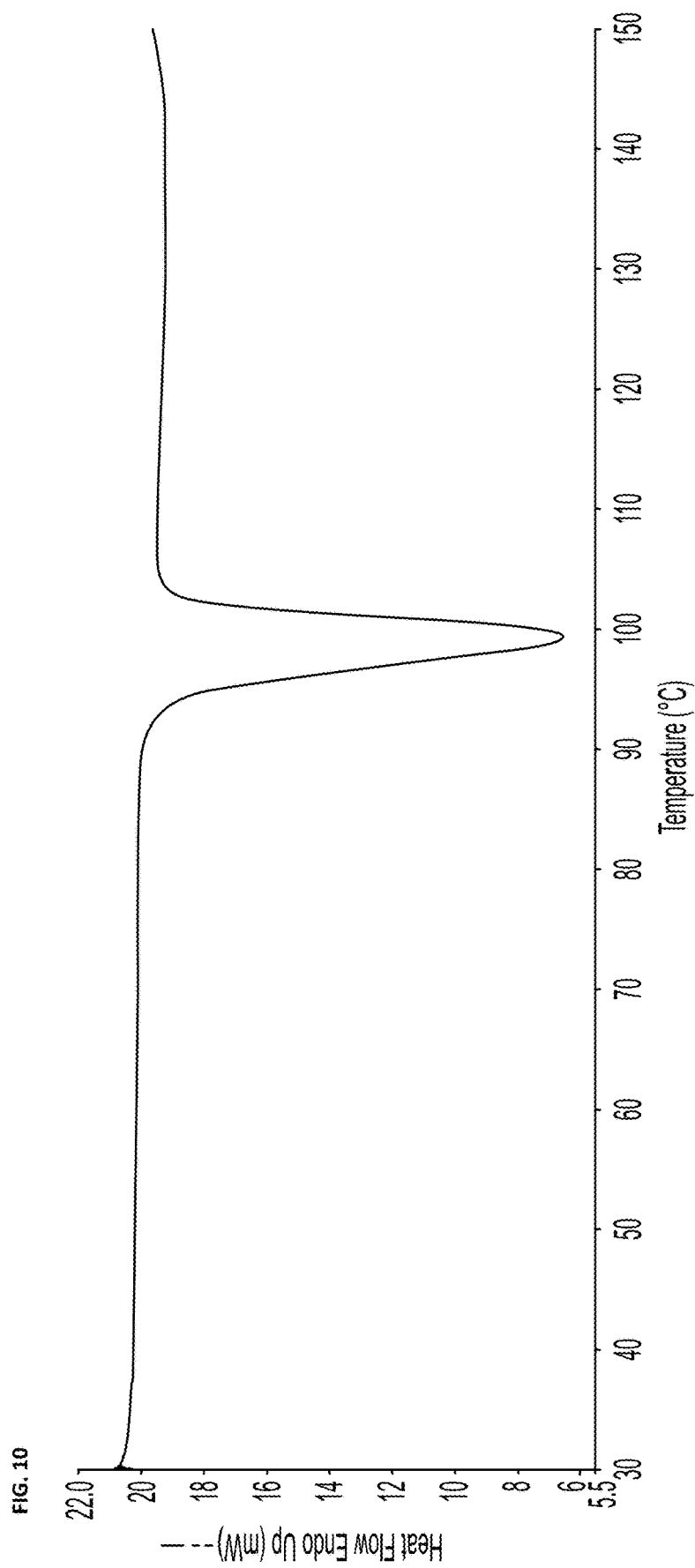
FIG. 10 shows a DSC trace for the 1:1 benzamide maleic acid cocrystal (Cocrystal 2).

The differential scanning calorimetry (DSC) trace of Cocrystal 2, FIG. 10, shows a single endotherm with an onset temperature of 94.6° C. and a peak maximum of 99.5° C.

TGA of Cocrystal 2

Figure 11:
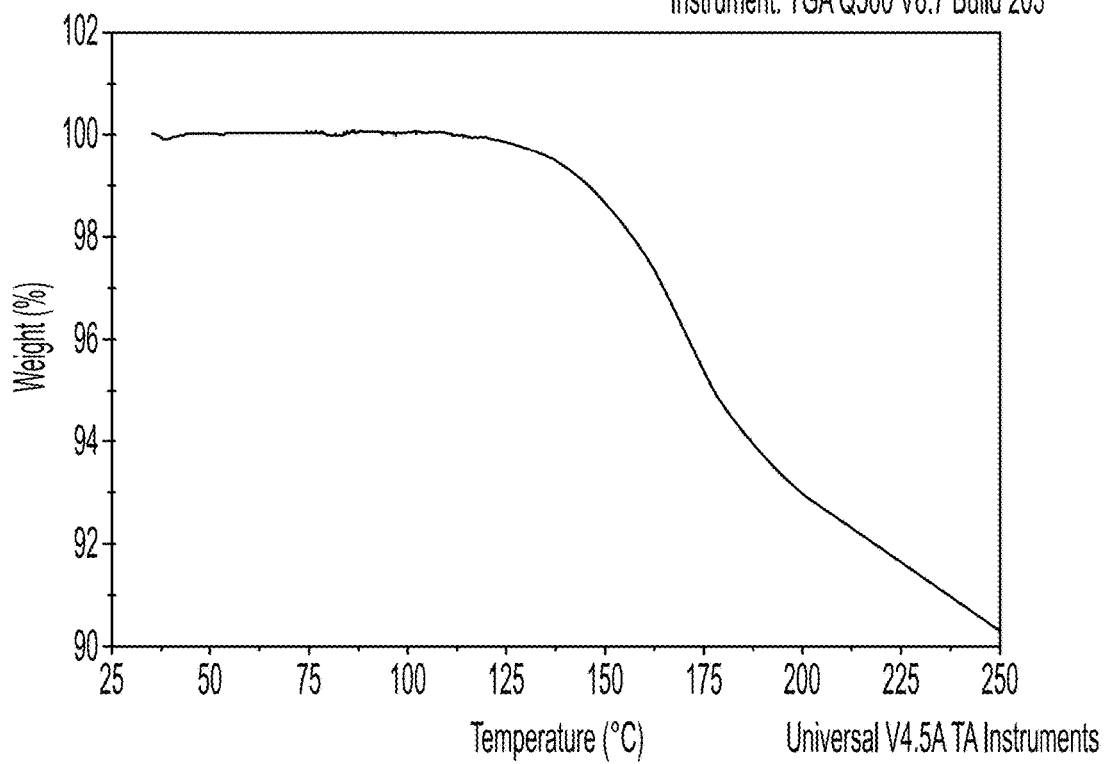
FIG. 11 shows a TGA trace for the 1:1 benzamide maleic acid cocrystal (Cocrystal 2).

The thermal gravimetric analysis (TGA) trace of Cocrystal 2, FIG. 11, shows that there is no significant weight loss prior to 125° C. The TGA indicates that the cocrystal is anhydrous.

¹H NMR Spectrum of Cocrystal 2

Figure 12:
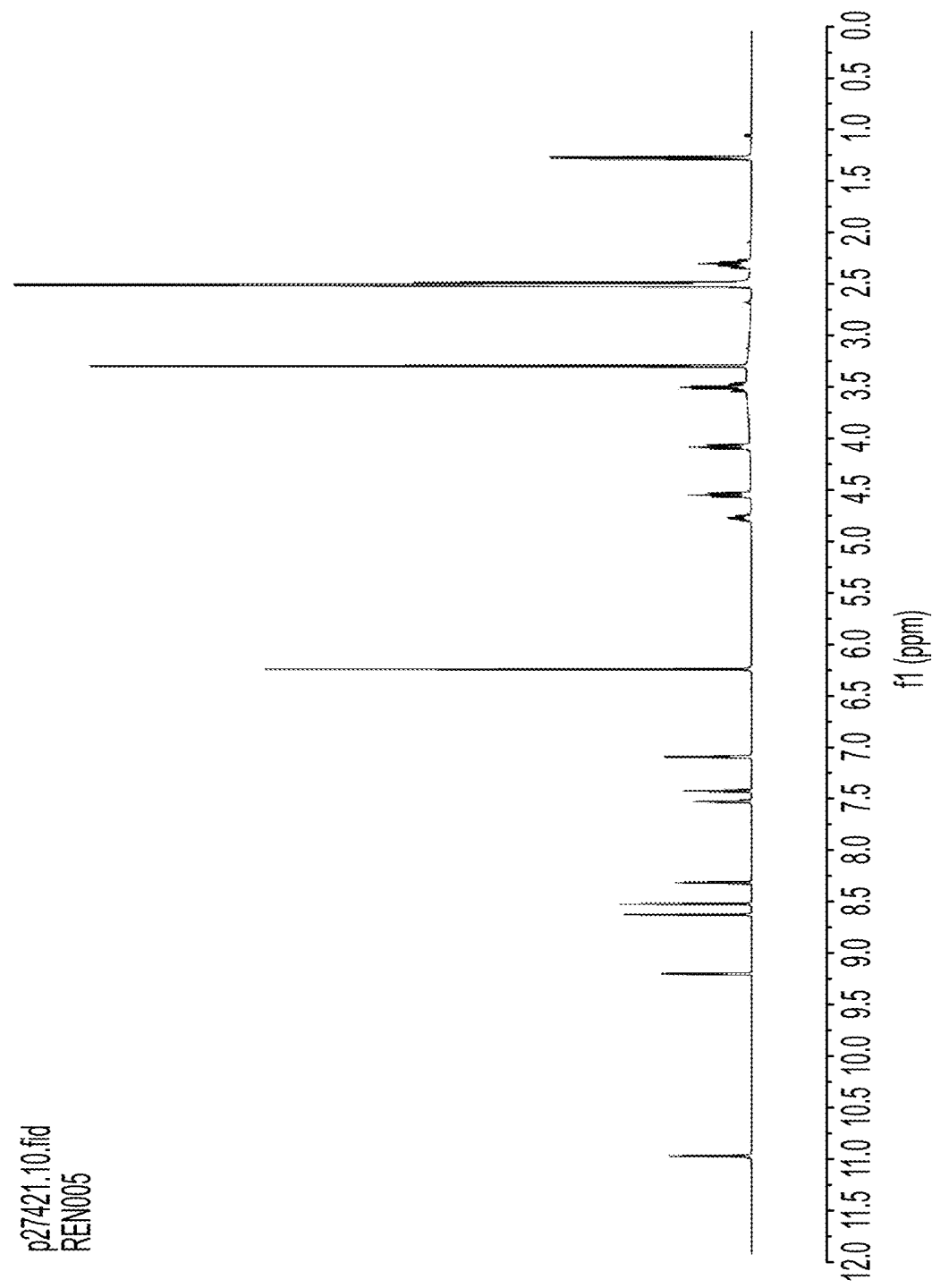
FIG. 12 shows the $^1$H NMR spectrum of 1:1 benzamide maleic acid cocrystal (Cocrystal 2).

The ¹H NMR spectrum of Cocrystal 2, shown in FIG. 12, displays the following peaks: ¹H NMR (400 MHz, DMSO): δ 1.24-126 (3H), 2.27-2.32 (2H), 2.48 (3H), 3.30 (3H), 3.46-3.55 (2H), 4.06-4.12 (2H), 4.52-4.59 (2H), 4.74-4.84 (1H), 6.27 (2H), 7.10-7.14 (1H), 7.45-7.49 (1H), 7.55-7.58 (1H), 8.34-8.39 (1H), 8.55-8.59 (1H), 8.66-8.7-(1H), 9.25-9.27 (1H) and 11.05 (1H). The peak at 6.27 ppm in the ¹H NMR spectrum corresponds to two protons of maleic acid. Comparison of the integration of this peak with that at 7.10-7.14, which corresponds to one proton of AZD1656, indicates that the cocrystal has as API:coformer stoichiometry of 1:1.

Polymorphism Study for Cocrystal 2

As AZD1656 is known to exist in six different crystalline forms an investigation was carried out to examine whether Cocrystal 2 could also exist in multiple polymorphic forms. Preparation methods 1 and 2 described above were carried out using 2-propanol, ethyl acetate, acetonitrile, methyl ethyl ketone and water. In all cases the same crystalline form of Cocrystal 2 was obtained indicating that this cocrystal exists as a single polymorphic form.

Example 3: 1:1 Benzamide Malonic Acid Cocrystal (Cocrystal 3)

Preparation of Cocrystal 3

The batch of Cocrystal 3 used for characterisation was prepared as follows:

AZD1656 (140 mg, 0.29 mmol) and malonic acid (40 mg, 0.38 mmol) were placed in a glass vial and malonic acid saturated 2-propanol (2 ml) was added. The resulting slurry was placed in a shaker and matured for 24 hours (room temperature to 50° C. on an 8-hour cycle, heating to 50° C. for 4 hours and then cooling to room temperature for 4 hours). The product was then filtered under vacuum and reslurried in nitromethane (3 ml) for 24 hours before being filtered and dried in-vacuo at 40° C. overnight.

XRPD Characterisation of Cocrystal 3

Figure 13:
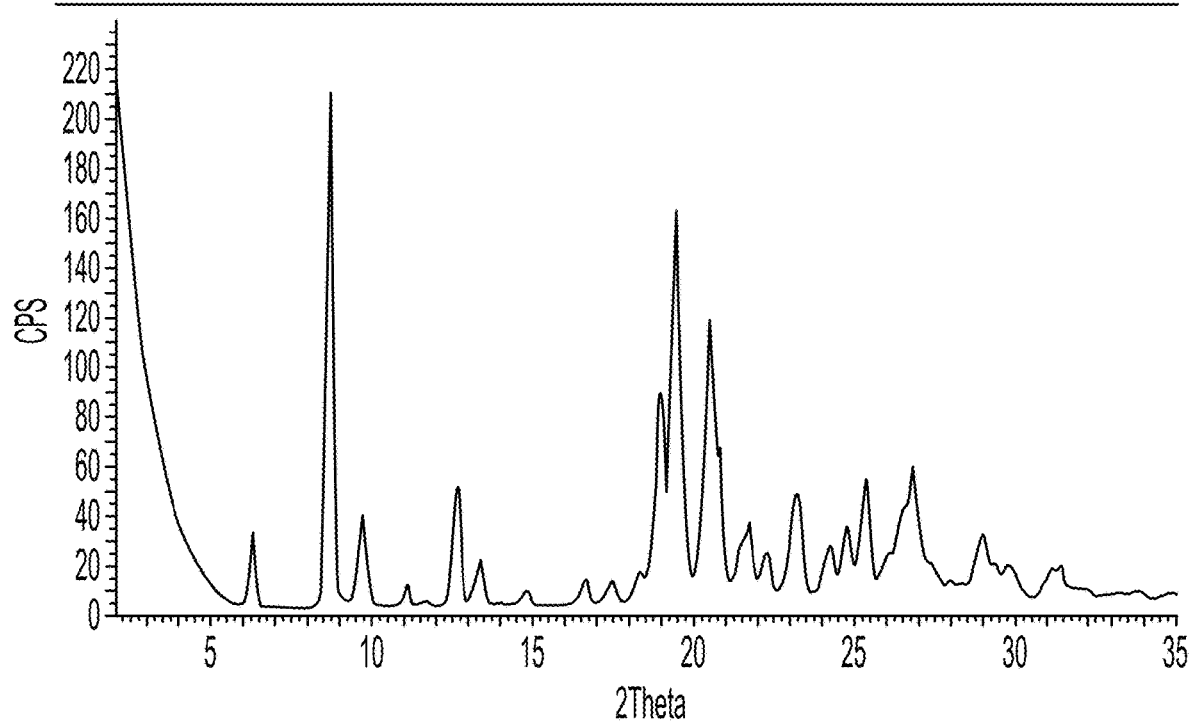
FIG. 13 shows an XRPD diagram of the 1:1 benzamide malonic acid cocrystal (Cocrystal 3).

The experimental XRPD pattern of Cocrystal 3 is shown in FIG. 13. Table 5 lists the angles, ° 2θ±0.2° 2θ, and d-spacing of the peaks identified in the experimental XRPD pattern of FIG. 13. The entire list of peaks, or a subset thereof, may be sufficient to characterize the cocrystal, as well as by an XRPD pattern substantially similar to FIG. 13. For example, the cocrystal may be characterized by at least two, at least three, at least four or all of the peaks selected from the peaks at 6.3, 8.7 9.7, 11.1, 12.6 and 13.4° 2θ±0.2° 2θ.

TABLE 5

| Angle<br>°2θ ± 0.2 °2θ | d value<br>Angstrom | Intensity<br>% |
|---|---|---|
| 6.3 | 14.08 | 13% |
| 8.7 | 10.17 | 100% |
| 9.7 | 9.14 | 17% |
| 11.1 | 7.99 | 4% |
| 12.6 | 7.01 | 24% |
| 13.4 | 6.62 | 9% |
| 14.8 | 5.98 | 2% |
| 16.6 | 5.33 | 5% |
| 17.5 | 5.08 | 4% |
| 18.3 | 4.84 | 5% |
| 19.0 | 4.68 | 44% |
| 19.4 | 4.56 | 83% |
| 20.5 | 4.33 | 58% |
| 21.7 | 4.09 | 15% |
| 22.3 | 3.99 | 9% |
| 23.2 | 3.83 | 21% |
| 24.2 | 3.67 | 10% |
| 24.8 | 3.59 | 14% |
| 25.4 | 3.51 | 25% |
| 26.0 | 3.42 | 14% |
| 26.5 | 3.36 | 30% |
| 26.8 | 3.33 | 29% |
| 29.0 | 3.08 | 14% |
| 29.8 | 3.00 | 7% |
| 31.4 | 2.85 | 7% |

DSC of Cocrystal 3

Figure 14:
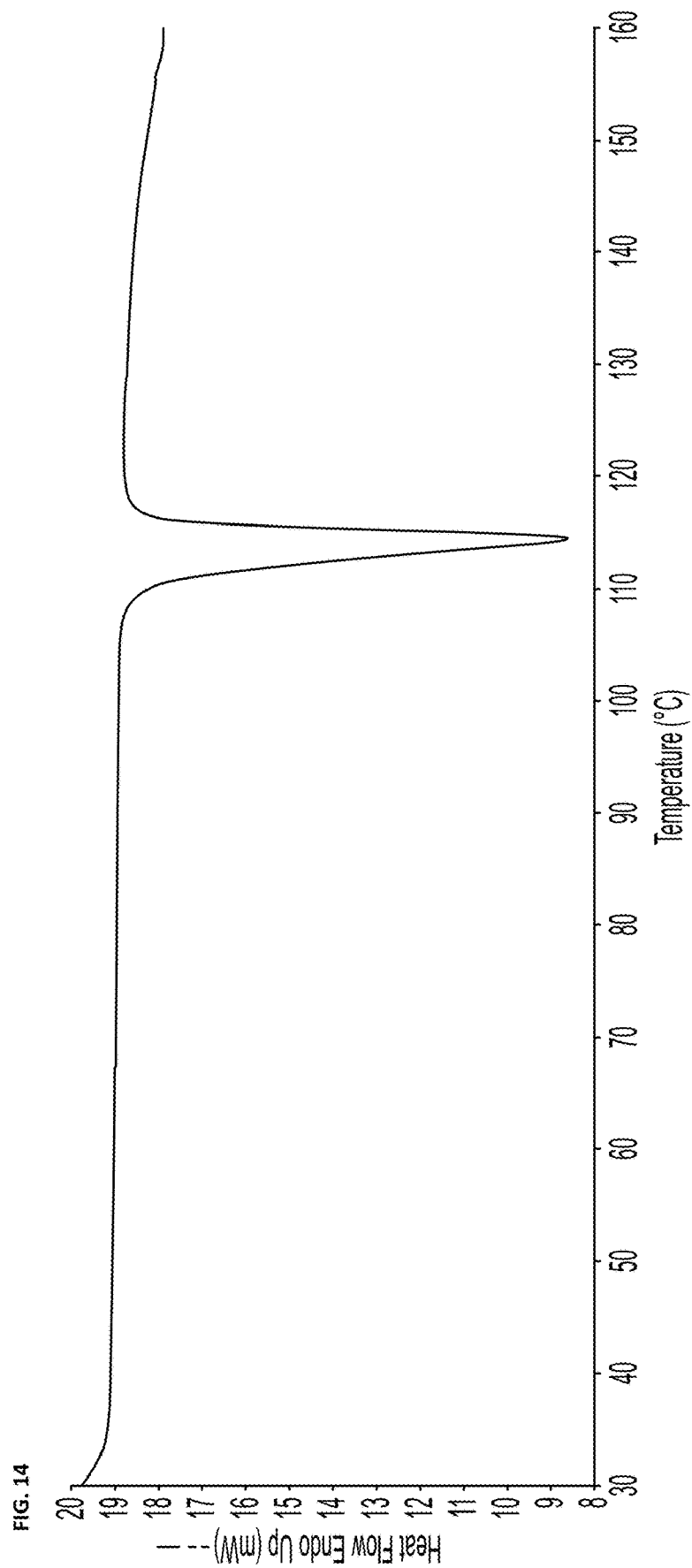
FIG. 14 shows a DSC trace for the 1:1 benzamide malonic acid cocrystal (Cocrystal 3).

The differential scanning calorimetry (DSC) trace of Cocrystal 3, FIG. 14, shows a single endotherm with an onset temperature of 111.2° C. and a peak maximum of 114.4° C.

¹H NMR Spectrum of Cocrystal 3

Figure 15:
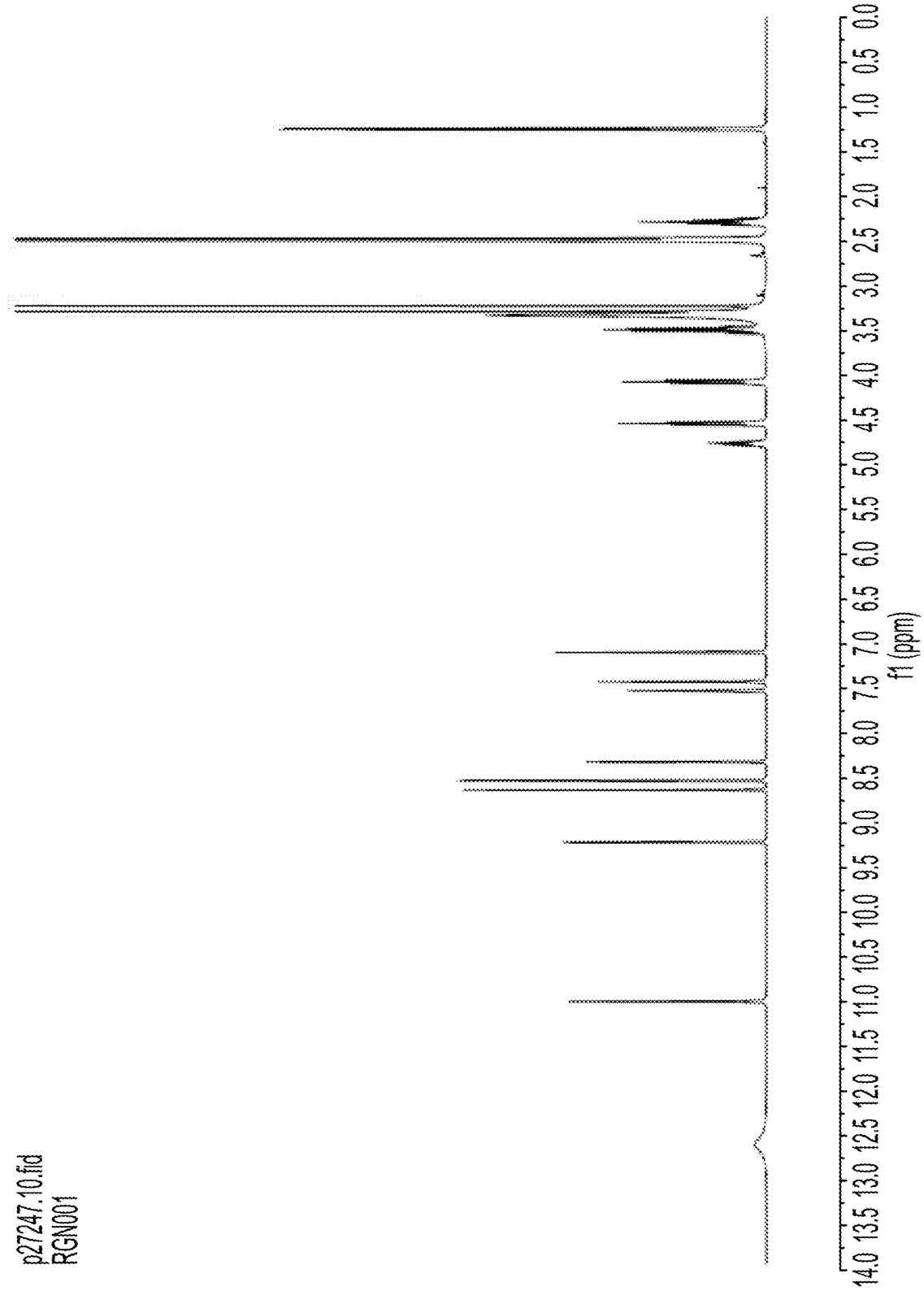
FIG. 15 shows the $^1$H NMR spectrum of 1:1 benzamide malonic acid cocrystal (Cocrystal 3).

The ¹H NMR spectrum of Cocrystal 3, shown in FIG. 15, displays the following peaks: 1H NMR (400 MHz, DMSO): δ 1.24-1.26 (3H), 2.27-2.32 (2H), 2.48 (3H), 3.24 (2H), 3.30 (3H), 3.46-3.55 (2H), 4.06-4.12 (2H), 4.52-4.59 (2H), 4.74-4.84 (1H), 7.10-7.14 (1H), 7.45-7.49 (1H), 7.55-7.58 (1H), 8.34-8.39 (1H), 8.55-8.59 (1H), 8.66-8.70 (1H), 9.25-9.27 (1H), 11.05 (1H) and 12.66 (2H). The peak at 3.24 ppm in the ¹H NMR spectrum corresponds to two protons of malonic acid. Comparison of the integration of this peak with that at 7.10-7.14, which corresponds to one proton of AZD1656, indicates that the cocrystal has as API:coformer stoichiometry of 1:1.

Example 4: 1:1 Benzamide L-Tartaric Acid Hydrate Cocrystal (Cocrystal 4)

Preparation of Cocrystal 4

The batch of Cocrystal 4 used for characterisation was prepared as follows:

AZD1656 (140 mg, 0.29 mmol) and L-tartaric acid (41 mg, 0.27 mmol) were dissolved at 40° C. in 2-propanol (2 ml) saturated with L-tartaric acid. Storage of the solution at 4° C. resulted in a white precipitate. The slurry was placed in a shaker and matured for 3 days (room temperature to 40° C. on an 8-hour cycle, heating to 40° C. for 4 hours and then cooling to room temperature for 4 hours). After this time the solid was filtered and dried in-vacuo at 40° C. overnight. Initial analysis showed that the product contained approximately 0.3 mol of 2-propanol. The solid was placed at 40° C./75% relative humidity (RH) for 2 weeks and then reanalysed showing that the 2-propanol had now been removed resulting in Cocrystal 4.

XRPD Characterisation of Cocrystal 4

Figure 16:
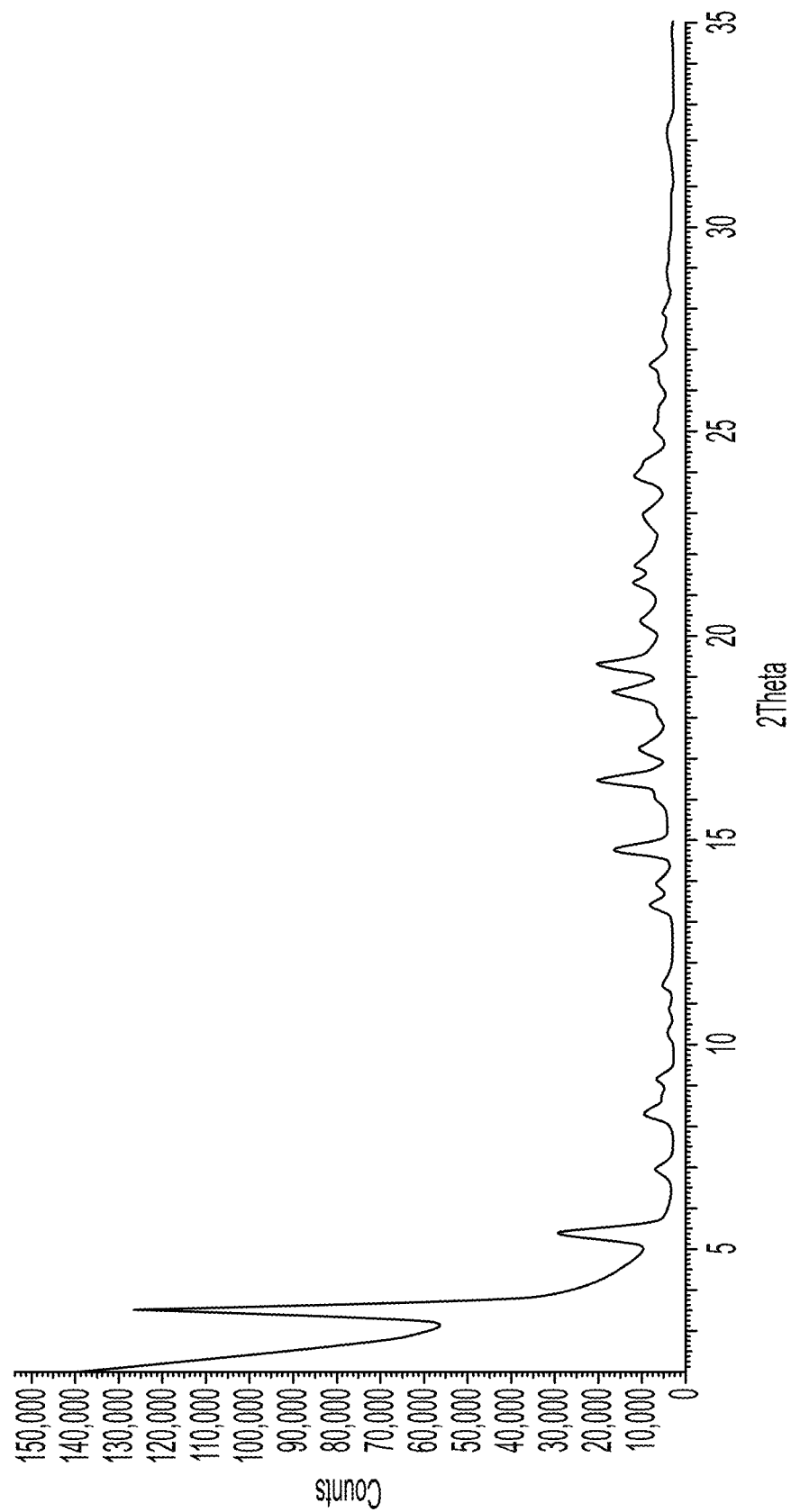
FIG. 16 shows an XRPD diagram of the 1:1 benzamide L-tartaric acid hydrate cocrystal (Cocrystal 4).

The experimental XRPD pattern of Cocrystal 4 is shown in FIG. 16. Table 6 lists the angles, ° 2θ±0.2° 2θ, and d-spacing of the peaks identified in the experimental XRPD pattern of FIG. 16. The entire list of peaks, or a subset thereof, may be sufficient to characterize the cocrystal, as well as by an XRPD pattern substantially similar to FIG. 16. For example, the cocrystal may be characterized by at least two, at least three, at least four or all of the peaks selected from the peaks at 3.5, 5.4, 14.8, 16.5, 18.6 and 19.3° 2θ±0.2° 2θ.

TABLE 6

| Angle °2θ ± 0.2 °2θ | d value Angstrom | Intensity % |
|---|---|---|
| 3.5 | 25.26 | 100% |
| 5.4 | 16.48 | 27% |
| 6.9 | 12.78 | 4% |
| 8.3 | 10.62 | 9% |
| 9.1 | 9.67 | 5% |
| 11.5 | 7.71 | 3% |
| 13.4 | 6.59 | 7% |
| 13.9 | 6.35 | 4% |
| 14.8 | 5.99 | 19% |
| 16.5 | 5.38 | 25% |
| 17.2 | 5.14 | 9% |
| 18.6 | 4.77 | 18% |
| 19.3 | 4.60 | 24% |
| 20.4 | 4.35 | 7% |
| 21.3 | 4.17 | 11% |
| 21.7 | 4.09 | 10% |
| 23.0 | 3.87 | 7% |
| 23.9 | 3.72 | 11% |
| 24.1 | 3.68 | 7% |
| 25.1 | 3.55 | 4% |
| 25.5 | 3.49 | 2% |
| 26.6 | 3.34 | 6% |

DSC of Cocrystal 4

Figure 17:
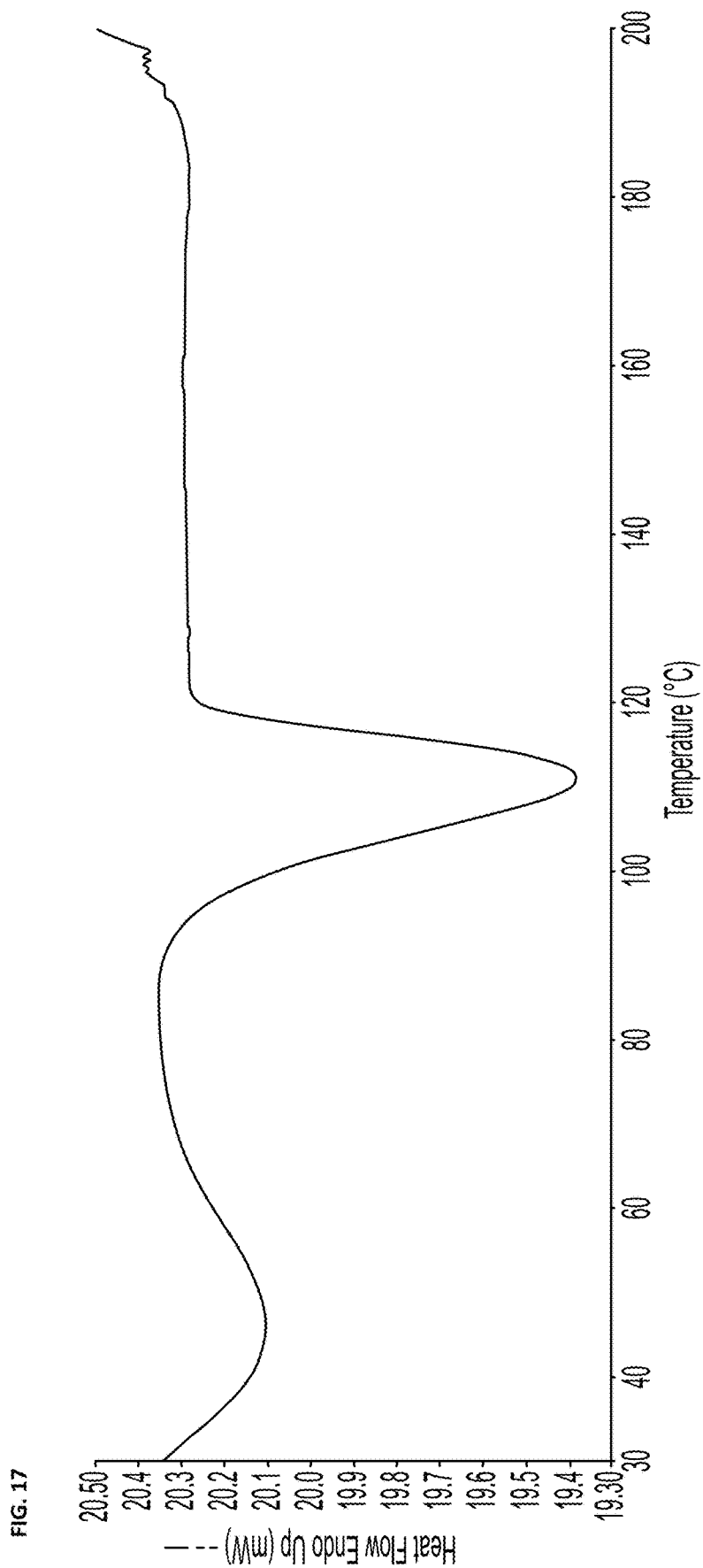
FIG. 17 shows a DSC trace for the 1:1 benzamide L-tartaric acid hydrate cocrystal (Cocrystal 4).

The differential scanning calorimetry (DSC) trace of Cocrystal 4, FIG. 17, shows a broad endotherm between 30° C. and 70° C. followed by a second endotherm with an onset temperature of 97.5° C. and a peak maximum of 111.0° C.

TGA of Cocrystal 4

Figure 18:
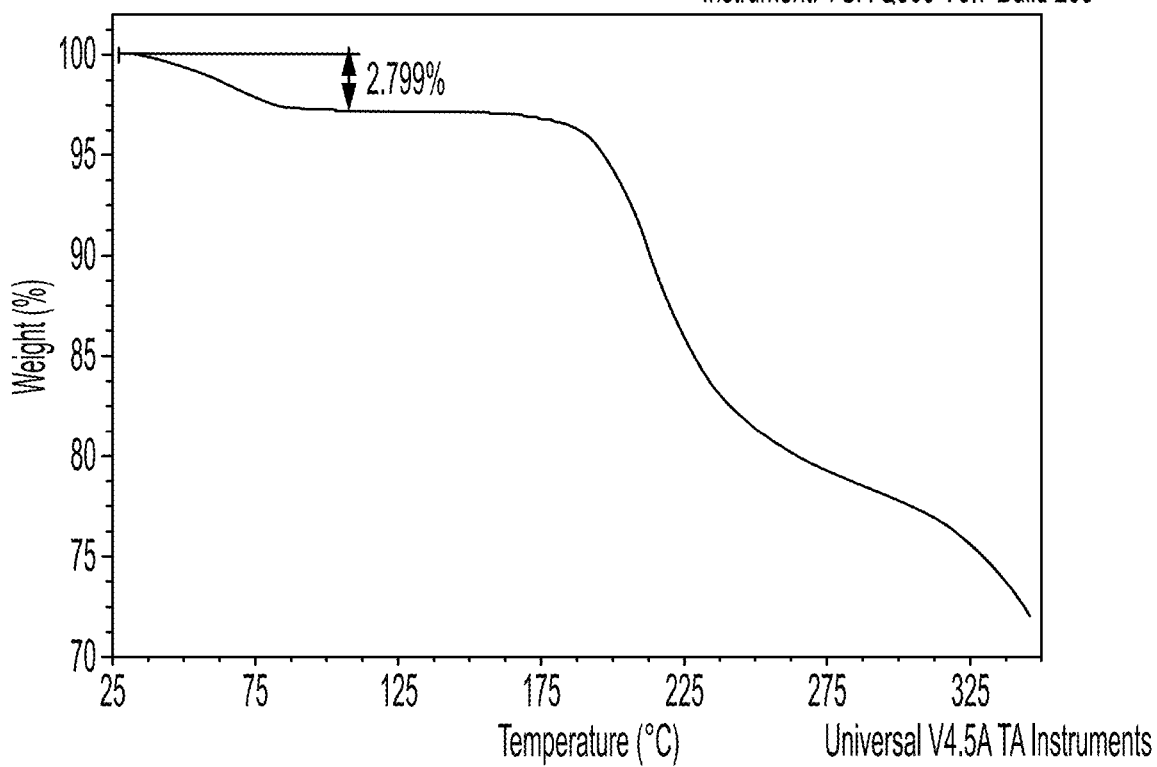
FIG. 18 shows a TGA trace for the 1:1 benzamide L-tartaric acid hydrate cocrystal (Cocrystal 4).

The thermal gravimetric analysis (TGA) trace of Cocrystal 4, FIG. 18, shows weight loss of 2.8% between 25° C. and 90° C. This corresponds to one mole of water.

$^1$H NMR Spectrum of Cocrystal 4

Figure 19:
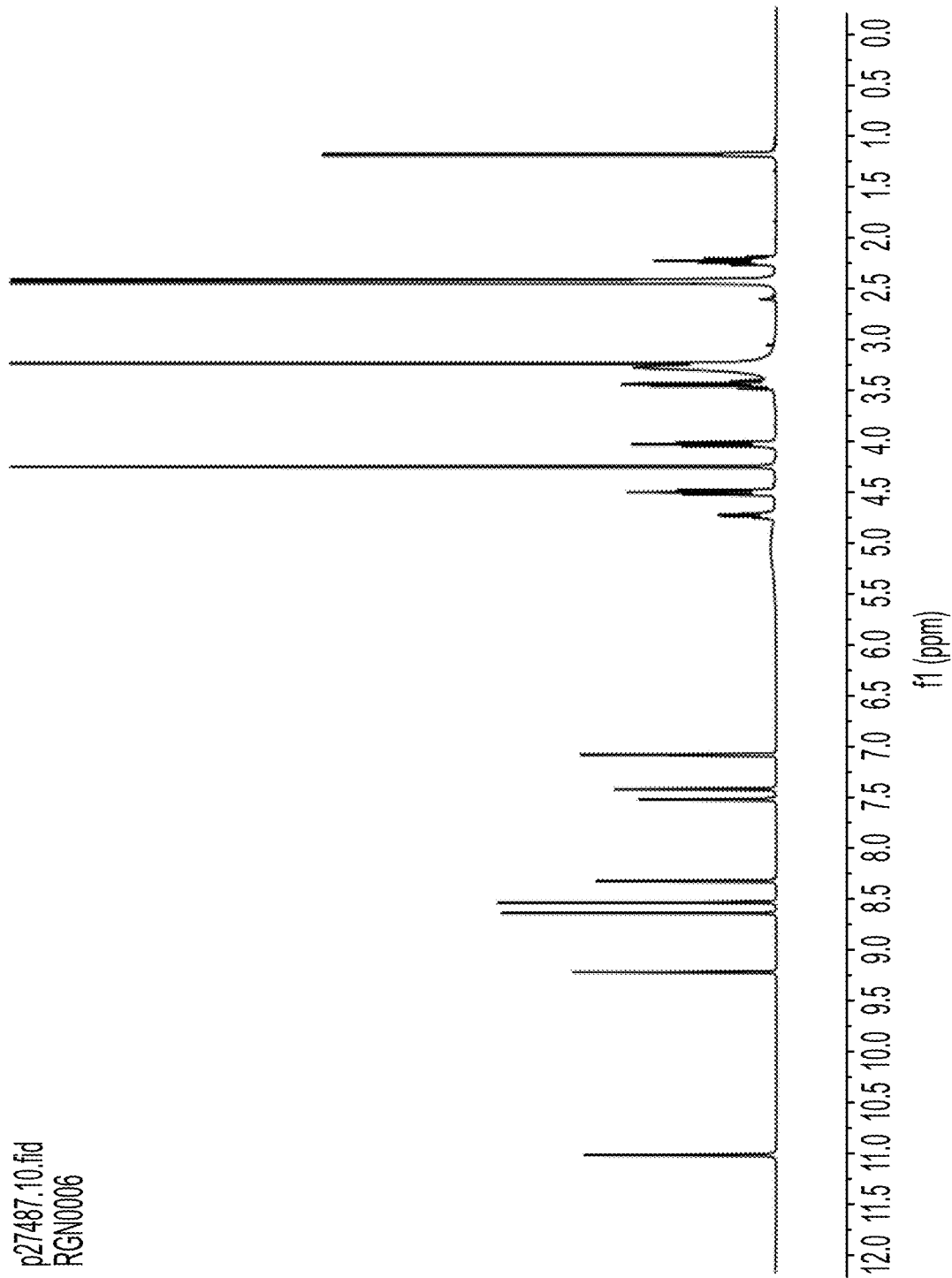
FIG. 19 shows the $^1$H NMR spectrum of 1:1 benzamide L-tartaric acid hydrate cocrystal (Cocrystal 4).

The $^1$H NMR spectrum of Cocrystal 4 shown in FIG. 19 displays the following peaks: 1H NMR (400 MHz, DMSO): δ 1.24-1.26 (3H), 2.27-2.32 (2H), 2.48 (3H), 3.30 (3H), 3.46-3.55 (2H), 4.06-4.12 (2H), 4.31 (2H), 4.52-4.59 (2H), 4.74-4.84 (1H), 7.10-7.14 (1H), 7.45-7.49 (1H), 7.55-7.58 (1H), 8.34-8.39 (1H), 8.55-8.59 (1H), 8.66-8.70 (1H), 9.25-9.27 (1H) and 11.05 (1H). The peak at 4.31 ppm in the $^1$H NMR spectrum corresponds to two protons of tartaric acid. Comparison of the integration of this peak with that at 4.74-4.84, which corresponds to one proton of AZD1656, indicates that the cocrystal has as API:coformer stoichiometry of 1:1.

Example 5: 1:1 Benzamide Gentisic Acid Cocrystal Form 1 (Cocrystal 5A)

Preparation of Cocrystal 5A

The batch of cocrystal 5A used for characterisation was prepared as follows:

AZD1656 (140 mg, 0.29 mmol) and gentisic acid (44 mg, 0.29 mmol) were placed in a glass vial and nitromethane (2 ml) was added. The resulting slurry was placed in a shaker and matured for 3 days (room temperature to 50° C. on an 8-hour cycle, heating to 50° C. for 4 hours and then cooling to room temperature for 4 hours). The product was then filtered under vacuum and dried in-vacuo at 60° C. overnight.

XRPD Characterisation of Cocrystal 5A

Figure 20:
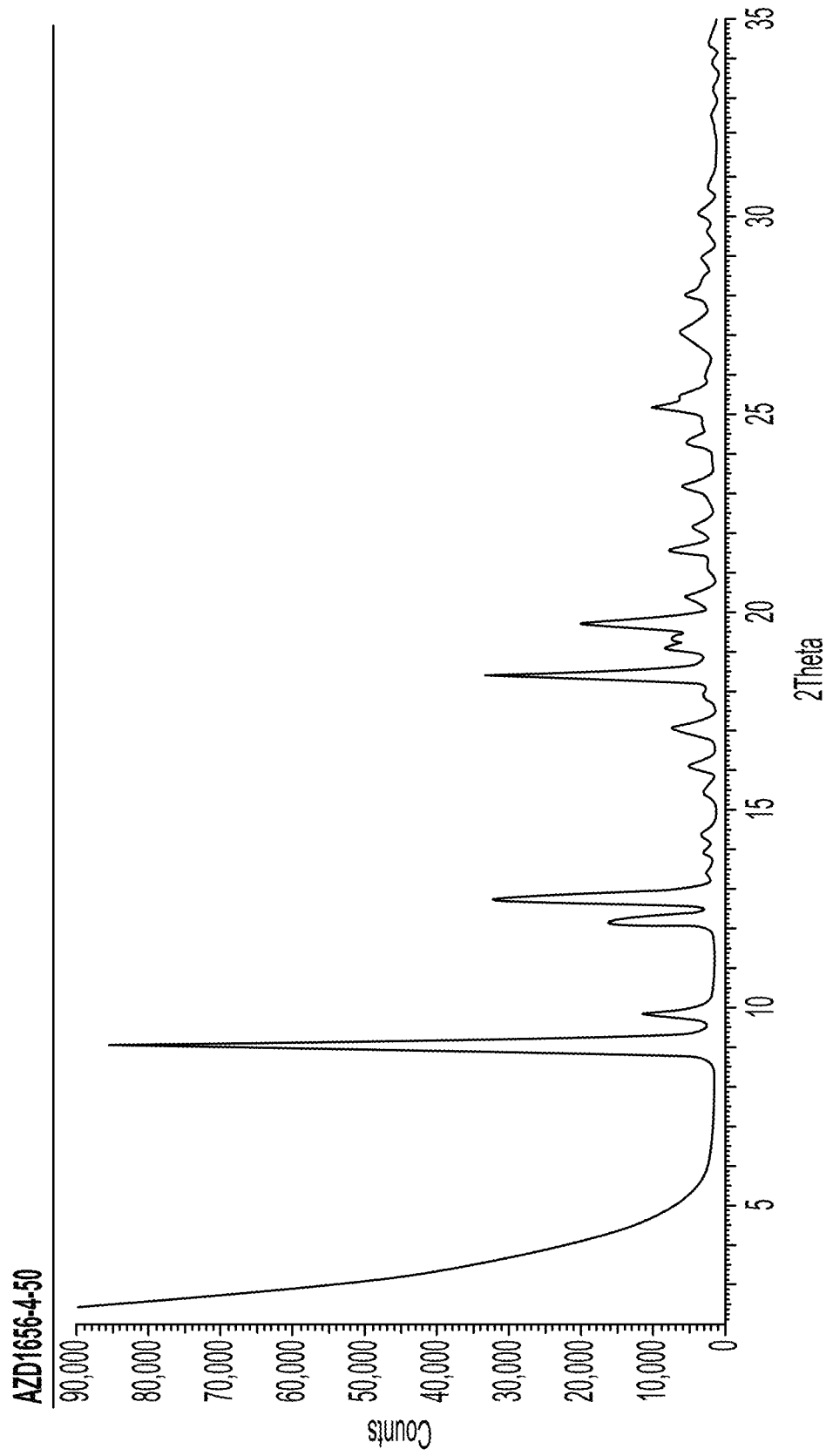
FIG. 20 shows an XRPD diagram of the 1:1 benzamide gentisic acid cocrystal Form 1 (Cocrystal 5A).

The experimental XRPD pattern of Cocrystal 5A is shown in FIG. 20. Table 7 lists the angles, ° 2θ±0.2° 2θ, and d-spacing of the peaks identified in the experimental XRPD pattern of FIG. 20. The entire list of peaks, or a subset thereof, may be sufficient to characterize the cocrystal, as well as by an XRPD pattern substantially similar to FIG. 20. For example, the cocrystal may be characterized by at least two, at least three, at least four or all of the peaks selected from the peaks at 9.1, 9.9, 12.2, 12.8, 18.4 and 19.7° 2θ±0.2° 2θ.

TABLE 7

| Angle °2θ ± 0.2 °2θ | d value Angstrom | Intensity % |
|---|---|---|
| 9.1 | 9.75 | 100% |
| 9.9 | 8.97 | 11% |
| 12.2 | 7.25 | 18% |
| 12.8 | 6.92 | 37% |
| 14.4 | 6.15 | 2% |
| 15.5 | 5.73 | 2% |
| 16.1 | 5.49 | 5% |
| 17.1 | 5.18 | 7% |
| 17.9 | 4.96 | 2% |
| 18.4 | 4.81 | 41% |
| 19.1 | 4.64 | 9% |
| 19.7 | 4.50 | 22% |
| 20.4 | 4.35 | 5% |
| 21.6 | 4.11 | 8% |
| 22.2 | 4.01 | 3% |
| 23.2 | 3.82 | 6% |
| 24.3 | 3.65 | 4% |
| 25.2 | 3.53 | 12% |
| 25.5 | 3.49 | 6% |
| 27.1 | 3.29 | 6% |
| 28.1 | 3.18 | 5% |
| 29.0 | 3.08 | 2% |
| 30.1 | 2.96 | 3% |

DSC of Cocrystal 5A

Figure 21:
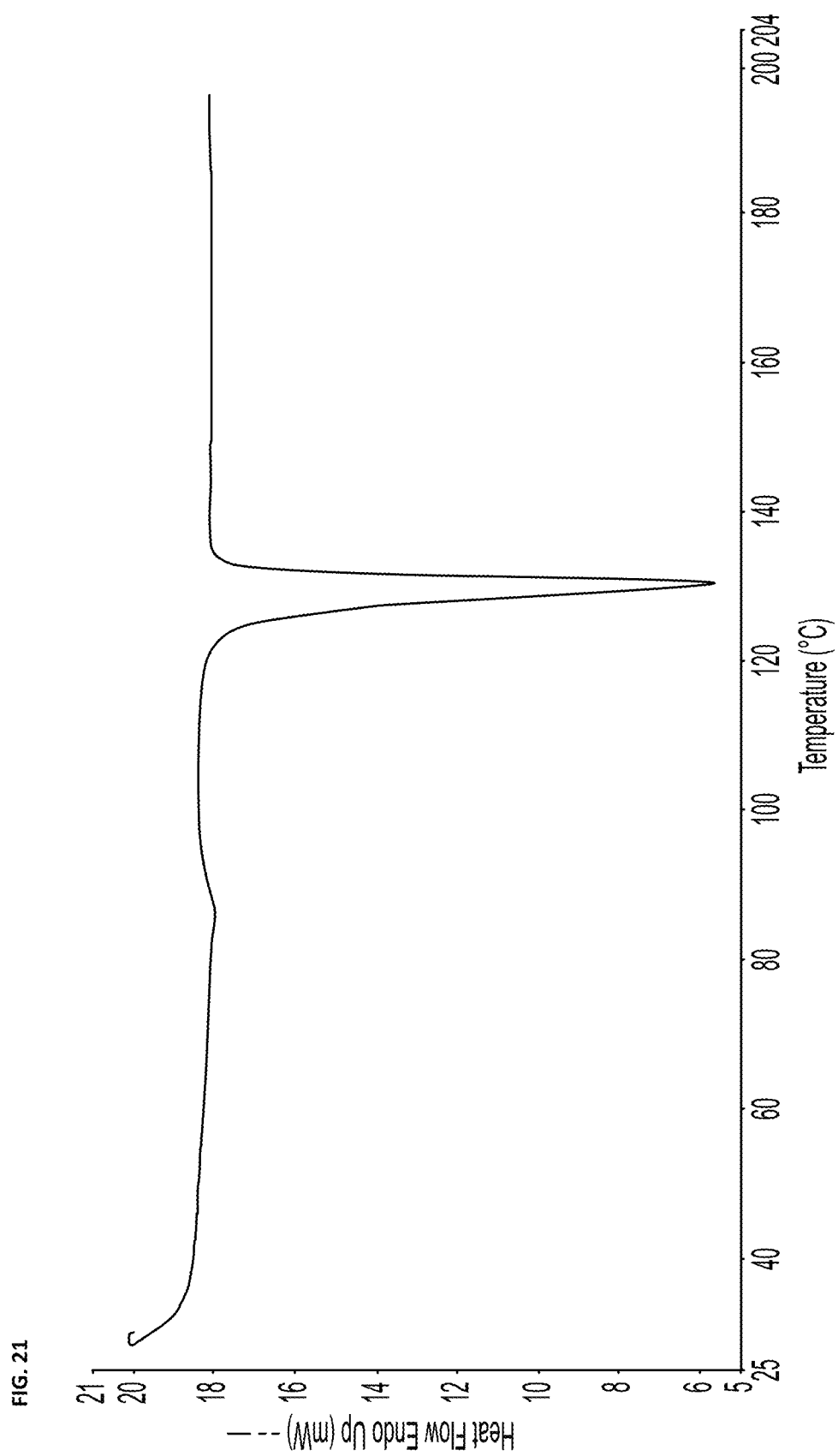
FIG. 21 shows a DSC trace for the 1:1 benzamide gentisic acid cocrystal Form 1 (Cocrystal 5A).

The differential scanning calorimetry (DSC) trace of Cocrystal 5A, FIG. 21, shows a major endotherm with an onset temperature of 128.1° C. and a peak maximum of 131.5° C.

TGA of Cocrystal 5A

Figure 22:
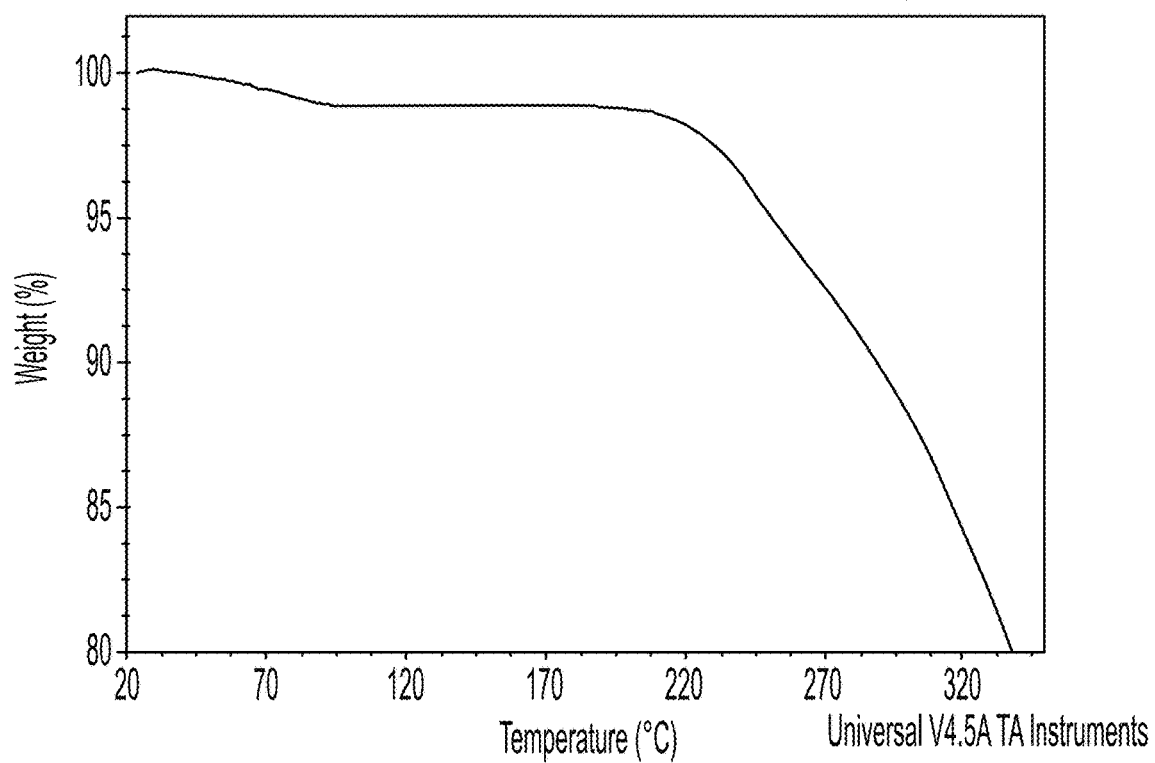
FIG. 22 shows a TGA trace for the 1:1 benzamide gentisic acid cocrystal Form 1 (Cocrystal 5A).

The thermal gravimetric analysis (TGA) trace of Cocrystal 5A, FIG. 22, shows weight loss of 1.3% between 25° C. and 90° C. This corresponds to 0.45 mole of water.

$^1$H NMR Spectrum of Cocrystal 5A

Figure 23:
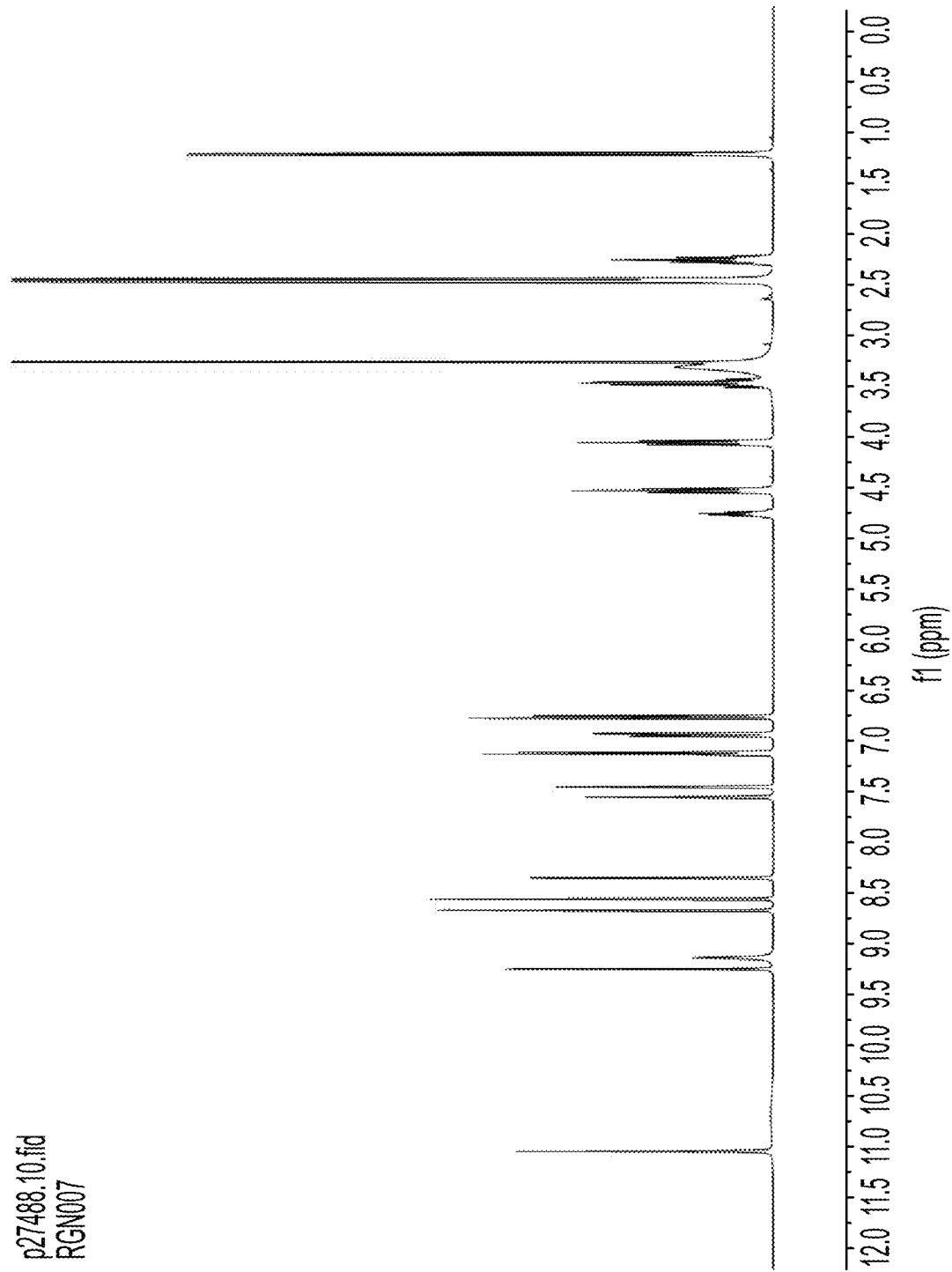
FIG. 23 shows the $^1$H NMR spectrum of 1:1 benzamide gentisic acid cocrystal Form 1 (Cocrystal 5A).

The $^1$H NMR spectrum of Cocrystal 5A, shown in FIG. 23, displays the following peaks: 1H NMR (400 MHz, DMSO): δ 1.24-1.26 (3H), 2.27-2.32 (2H), 2.48 (3H), 3.30 (3H), 3.46-3.55 (2H), 4.06-4.12 (2H), 4.52-4.59 (2H), 4.74-4.84 (1H), 6.77-6.79 (1H), 6.94-6.97 (1H), 7.10-7.14 (1H), 7.45-7.49 (1H), 7.55-7.58 (1H), 8.34-8.39 (1H), 8.55-8.59 (1H), 8.66-8.70 (1H), 9.14 (1H), 9.25-9.27 (1H) and 11.05

(1H). The peak at 6.77-6.79 ppm in the $^1$H NMR spectrum corresponds to one proton of gentisic acid. Comparison of the integration of this peak with that at 4.74-4.84, which corresponds to one proton of AZD1656, indicates that the cocrystal has as API:coformer stoichiometry of 1:1.

Example 6: 1:1 Benzamide Gentisic Acid Cocrystal Form 2 (Cocrystal 5B)

Preparation of Cocrystal 5B

The batch of Cocrystal 5B used for characterisation was prepared as follows:

AZD1656 (159 mg, 0.33 mmol) was placed in a glass vial and 2-propanol (1.5 ml) saturated with gentisic acid was added. Water (1 ml) was added and the resulting slurry was placed in a shaker and matured for 24 hours (room temperature to 50° C. on an 8-hour cycle, heating to 50° C. for 4 hours and then cooling to room temperature for 4 hours). The product was filtered under vacuum and then reslurried in nitromethane (3 ml) at room temperature for 24 hours before being filtered under vacuum and dried in-vacuo overnight at 40° C.

XRPD Characterisation of Cocrystal 5B

Figure 24:
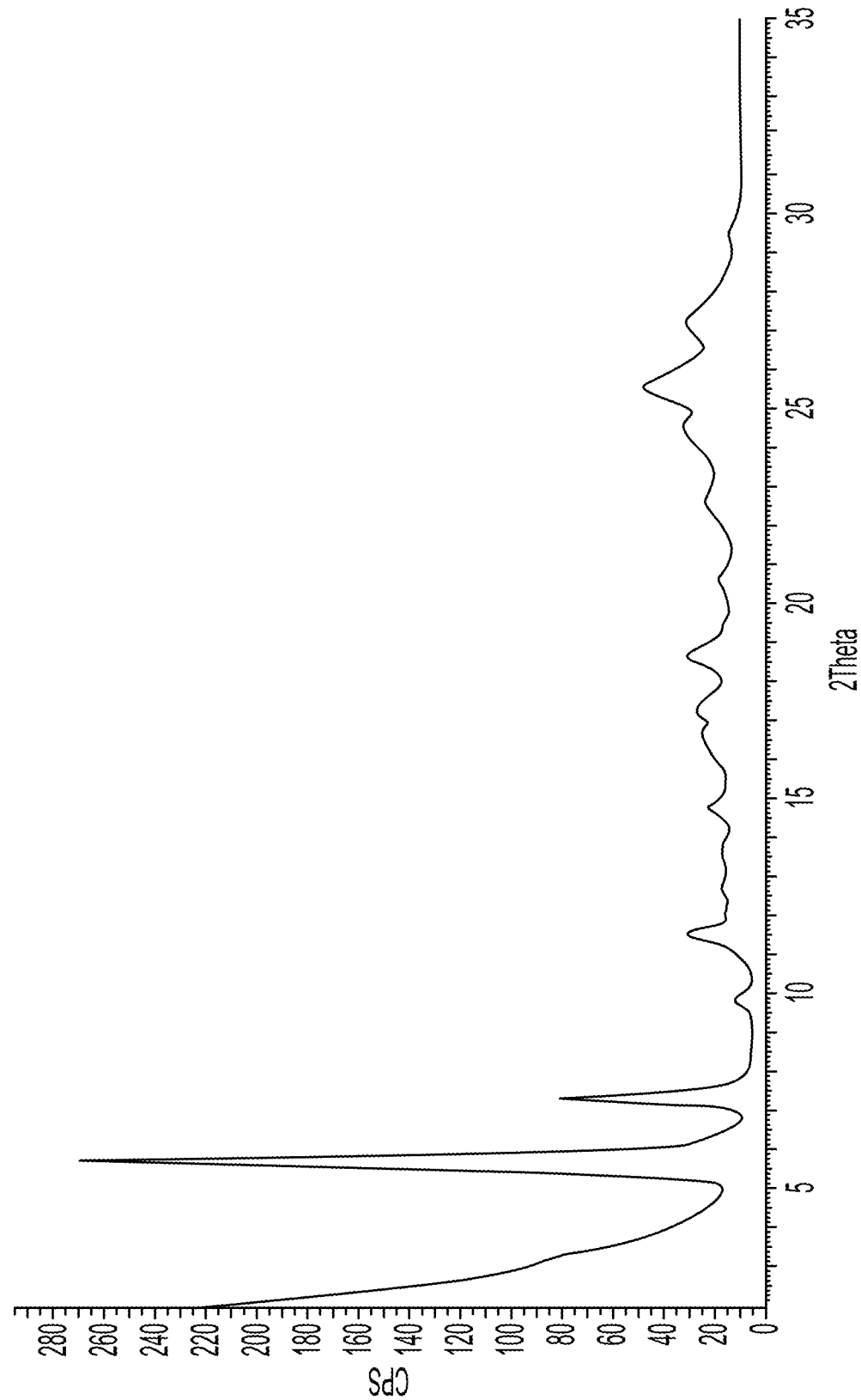
FIG. 24 shows an XRPD diagram of the 1:1 benzamide gentisic acid cocrystal Form 2 (Cocrystal 5B).

The experimental XRPD pattern of Cocrystal 5B is shown in FIG. 24. Table 8 lists the angles, ° 2θ±0.2° 2θ, and d-spacing of the peaks identified in the experimental XRPD pattern of FIG. 24. The entire list of peaks, or a subset thereof, may be sufficient to characterize the cocrystal, as well as by an XRPD pattern substantially similar to FIG. 24.

TABLE 8

| Angle °2θ ± 0.2 °2θ | d value Angstrom | Intensity % |
|---|---|---|
| 5.7 | 15.37 | 100% |
| 7.4 | 11.97 | 29% |
| 9.9 | 8.97 | 2% |
| 11.6 | 7.65 | 18% |
| 14.8 | 5.99 | 5% |
| 16.7 | 5.31 | 9% |
| 17.2 | 5.14 | 11% |
| 18.7 | 4.74 | 7% |
| 20.6 | 4.31 | 3% |
| 22.6 | 3.93 | 4% |
| 24.6 | 3.61 | 8% |
| 25.6 | 3.48 | 16% |
| 27.2 | 3.27 | 9% |

DSC of Cocrystal 5B

Figure 25:
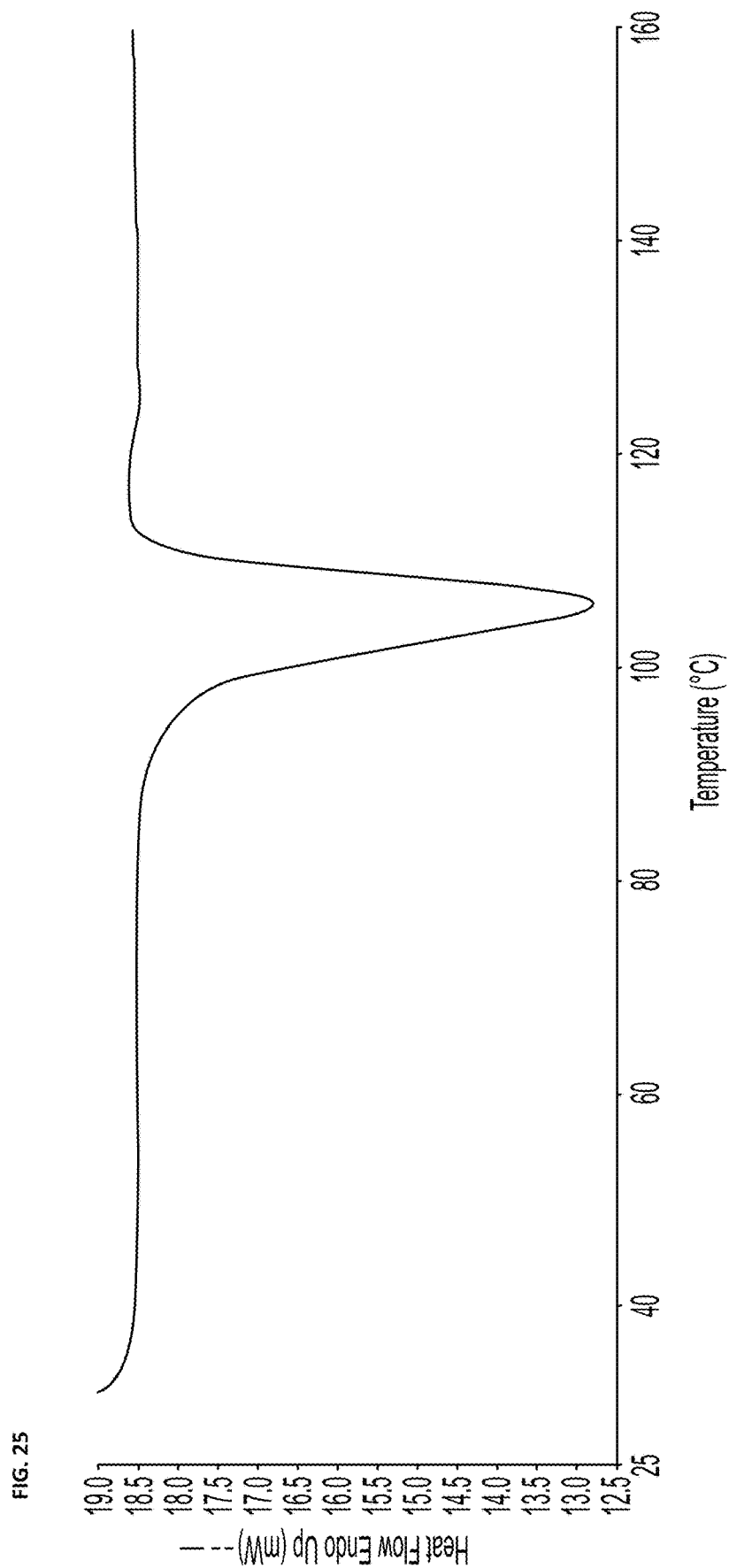
FIG. 25 shows a DSC trace for the 1:1 benzamide gentisic acid cocrystal Form 2 (Cocrystal 5B).

The differential scanning calorimetry (DSC) trace of Cocrystal 5B, FIG. 25, shows a single endotherm with an onset temperature of 98.2° C. and a peak maximum of 106.0° C.

$^1$H NMR Spectrum of Cocrystal 5B

Figure 26:
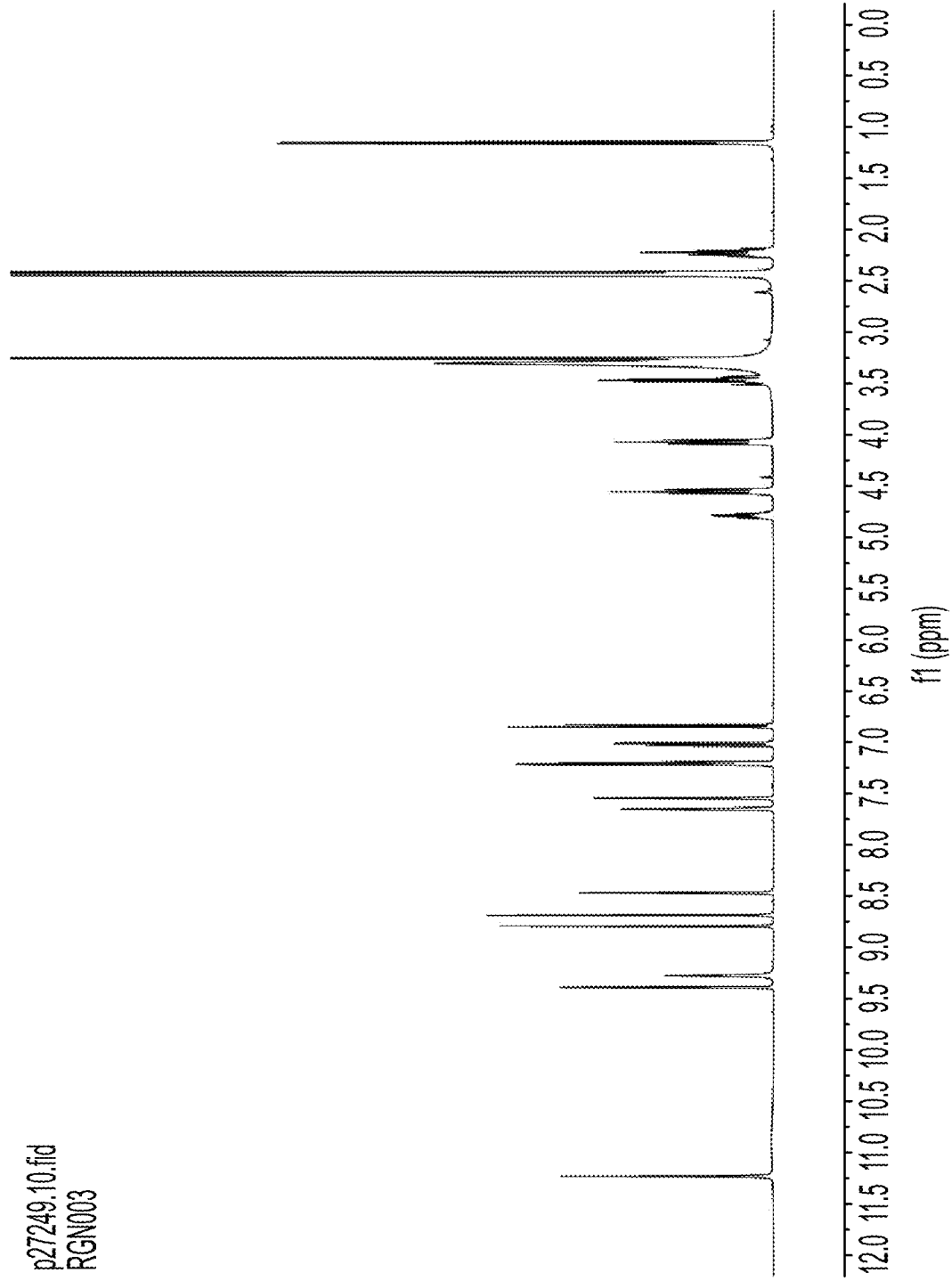
FIG. 26 shows the $^1$H NMR spectrum of 1:1 benzamide gentisic acid cocrystal Form 2 (Cocrystal 5B).

The $^1$H NMR spectrum of Cocrystal 5B, shown in FIG. 26, displays the following peaks: $^1$H NMR (400 MHz, DMSO): δ 1.24-1.26 (31H), 2.27-2.32 (21H), 2.48 (31H), 3.30 (31H), 3.46-3.55 (21H), 4.06-4.12 (21H), 4.52-4.59 (2H), 4.74-4.84 (1H), 6.77-6.79 (1H), 6.94-6.97 (1H), 7.10-7.14 (1H), 7.45-7.49 (1H), 7.55-7.58 (1H), 8.34-8.39 (1H), 8.55-8.59 (1H), 8.66-8.70 (1H), 9.14 (1H), 9.25-9.27 (1H) and 11.05 (1H). The peak at 6.77-6.79 ppm in the $^1$H NMR spectrum corresponds to one proton of gentisic acid. Comparison of the integration of this peak with that at 4.74-4.84, which corresponds to one proton of AZD1656, indicates that the cocrystal has as API:coformer stoichiometry of 1:1.

Example 7: 1:1 Benzamide Gentisic Acid Cocrystal Form 3 (Cocrystal 5C)

Preparation of Cocrystal 5C

The batch of Cocrystal 5C used for characterisation was prepared as follows:

AZD1656 (136 mg, 0.28 mmol) and gentisic acid (40 mg, 0.25 mmol) were placed in a glass vial and water (2 ml) saturated with gentisic acid was added. Water (1 ml) was added and the resulting slurry was placed in a shaker and matured for 4 days (room temperature to 50° C. on an 8-hour cycle, heating to 50° C. for 4 hours and then cooling to room temperature for 4 hours). The product was then filtered under vacuum and air dried for 4 hours.

XRPD Characterisation of Cocrystal 5C

Figure 27:
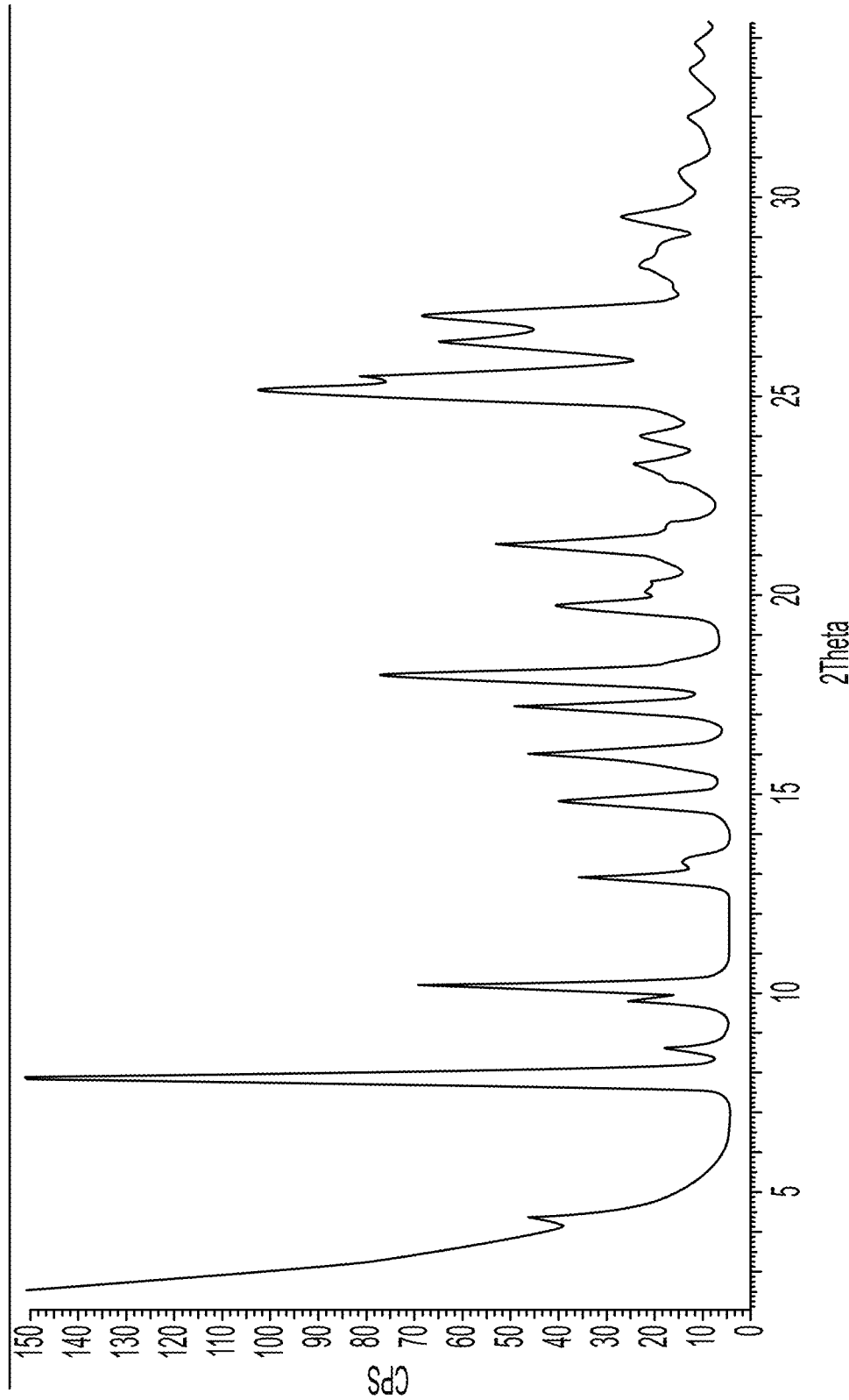
FIG. 27 shows an XRPD diagram of the 1:1 benzamide gentisic acid cocrystal Form 3 (Cocrystal 5C).

The experimental XRPD pattern of Cocrystal 5C is shown in FIG. 27. Table 9 lists the angles, ° 2θ±0.2° 2θ, and d-spacing of the peaks identified in the experimental XRPD pattern of FIG. 27. The entire list of peaks, or a subset thereof, may be sufficient to characterize the cocrystal, as well as by an XRPD pattern substantially similar to FIG. 27.

TABLE 9

| Angle °2θ ± 0.2 °2θ | d value Angstrom | Intensity % |
|---|---|---|
| 4.2 | 21.00 | 12% |
| 7.7 | 11.43 | 100% |
| 8.5 | 10.38 | 10% |
| 9.7 | 9.12 | 11% |
| 10.1 | 8.76 | 41% |
| 12.9 | 6.88 | 18% |
| 13.3 | 6.64 | 4% |
| 14.8 | 6.00 | 13% |
| 15.9 | 5.57 | 18% |
| 17.1 | 5.17 | 23% |
| 18.0 | 4.94 | 33% |
| 19.7 | 4.51 | 17% |
| 20.3 | 4.38 | 5% |
| 20.8 | 4.27 | 4% |
| 21.3 | 4.18 | 22% |
| 21.7 | 4.09 | 5% |
| 22.9 | 3.89 | 5% |
| 23.3 | 3.82 | 6% |
| 24.0 | 3.71 | 7% |
| 24.6 | 3.61 | 4% |
| 25.1 | 3.54 | 32% |
| 25.5 | 3.49 | 25% |
| 26.3 | 3.38 | 18% |
| 27.0 | 3.30 | 23% |
| 28.3 | 3.15 | 8% |
| 28.9 | 3.09 | 4% |
| 29.5 | 3.02 | 8% |

DSC of Cocrystal 5C

Figure 28:
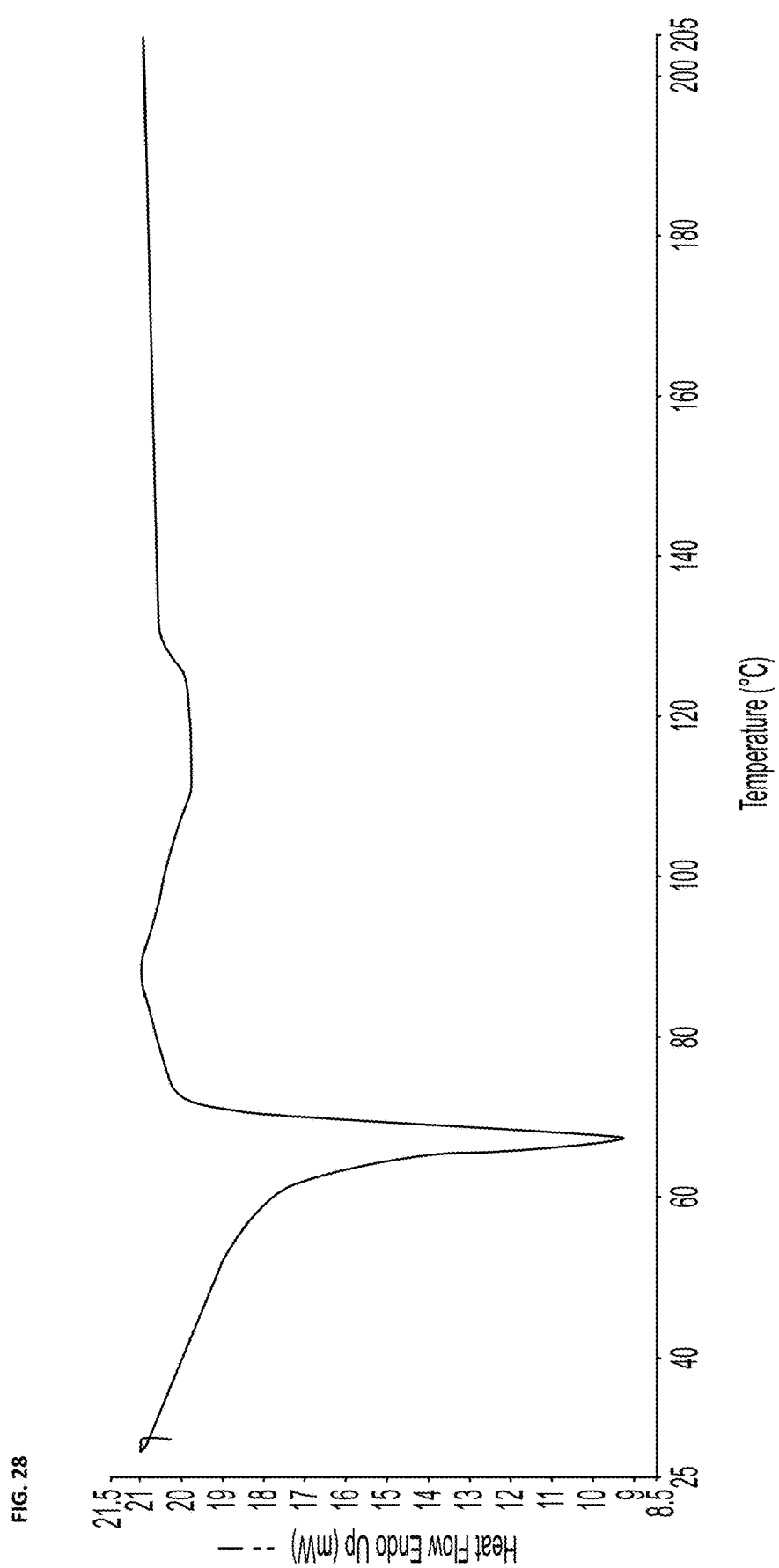
FIG. 28 shows a DSC trace for the 1:1 benzamide gentisic acid cocrystal Form 3 (Cocrystal 5C).

The differential scanning calorimetry (DSC) trace of Cocrystal 5C, FIG. 28, shows a major endotherm with a peak maximum of 67.4° C.

$^1$H NMR Spectrum of Cocrystal 5C

Figure 29:
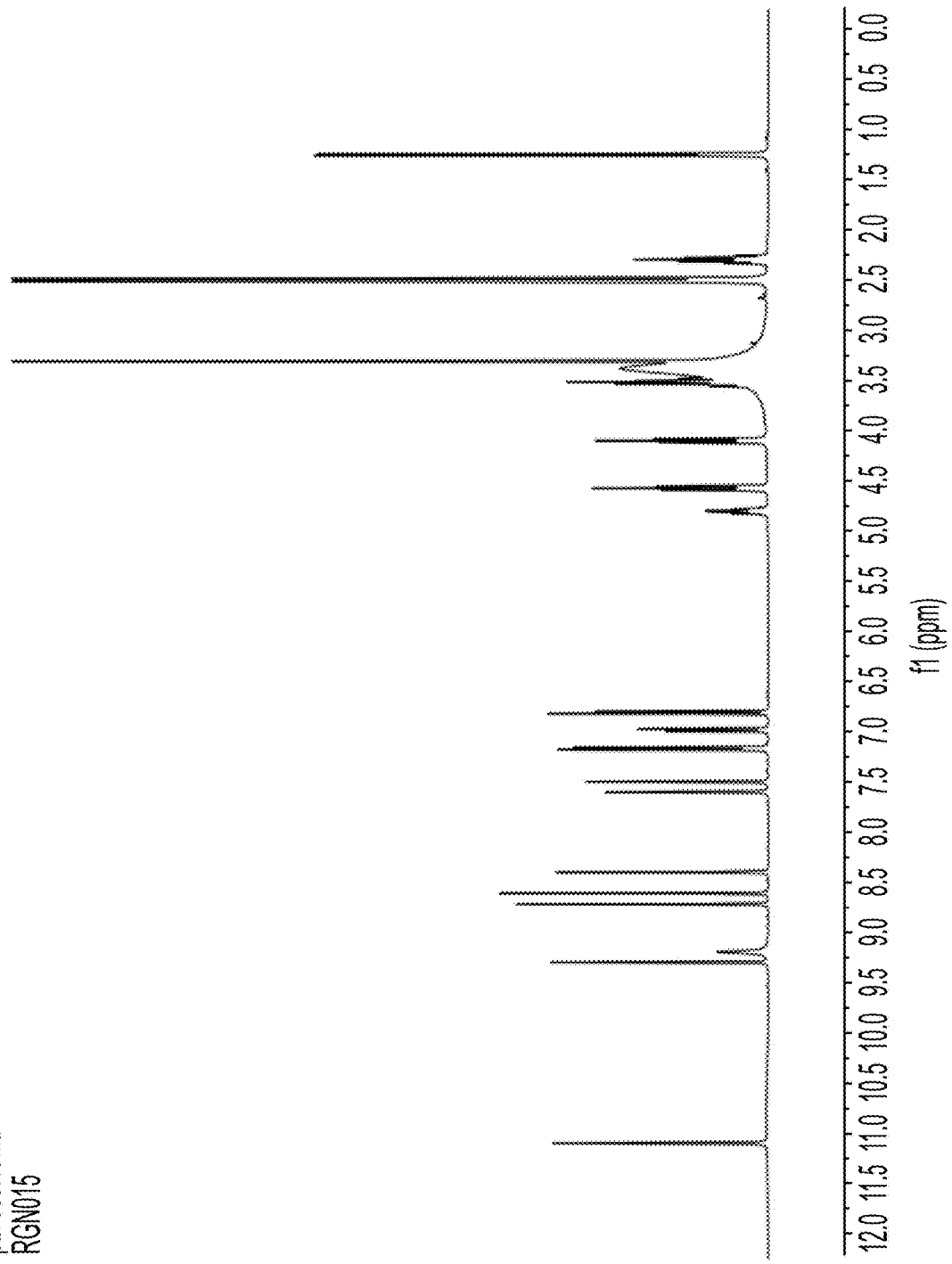
FIG. 29 shows the $^1$H NMR spectrum of 1:1 benzamide gentisic acid cocrystal Form 3 (Cocrystal 5C).

The $^1$H NMR spectrum of Cocrystal 5C, shown in FIG. 29, displays the following peaks: $^1$H NMR (400 MHz, DMSO): δ 1.24-1.26 (3H), 2.27-2.32 (2H), 2.48 (3H), 3.30 (3H), 3.46-3.55 (2H), 4.06-4.12 (2H), 4.52-4.59 (2H), 4.74-4.84 (1H), 6.77-6.79 (1H), 6.94-6.97 (1H), 7.10-7.14 (1H), 7.45-7.49 (1H), 7.55-7.58 (1H), 8.34-8.39 (1H), 8.55-8.59 (1H), 8.66-8.70 (1H), 9.14 (1H), 9.25-9.27 (1H) and 11.05 (1H). The peak at 6.77-6.79 ppm in the $^1$H NMR spectrum corresponds to one proton of gentisic acid. Comparison of the integration of this peak with that at 4.74-4.84, which corresponds to one proton of AZD1656, indicates that the cocrystal has as API:coformer stoichiometry of 1:1.

Example 8: 1:1 Benzamide Gentisic Acid Cocrystal Form 4 (Cocrystal 5D)

Preparation of Cocrystal 5D

The batch of Cocrystal 5D used for characterisation was prepared as follows:

Cocrystal 5C was dried in-vacuo at 50° C. for three hours resulting in conversion to Cocrystal 5D.

XRPD Characterisation of Cocrystal 5D

Figure 30:
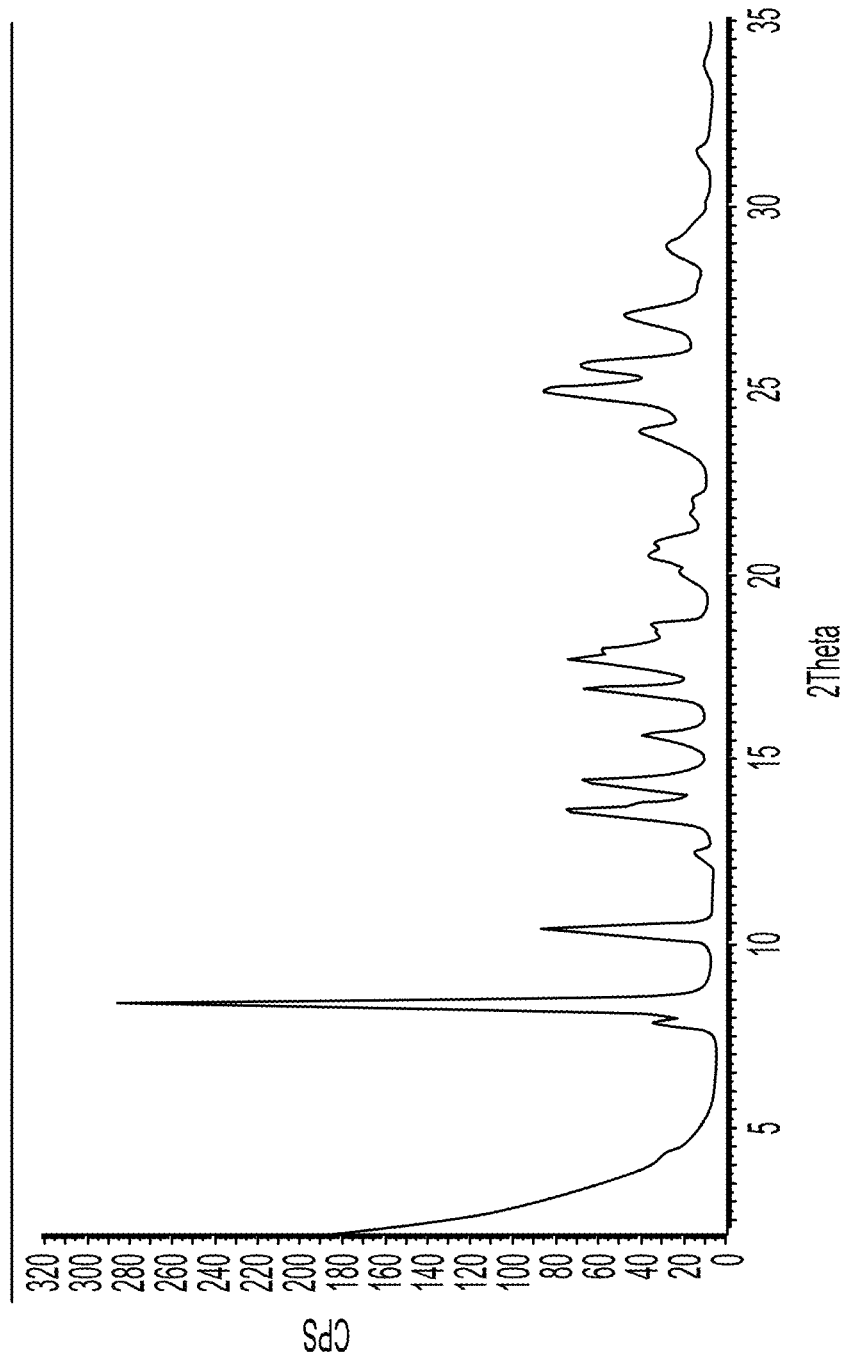
FIG. 30 shows an XRPD diagram of the 1:1 benzamide gentisic acid cocrystal Form 4 (Cocrystal 5D).

The experimental XRPD pattern of Cocrystal 5D is shown in FIG. 30. Table 10 lists the angles, ° 2θ±0.2° 2θ, and d-spacing of the peaks identified in the experimental XRPD pattern of FIG. 30. The entire list of peaks, or a subset thereof, may be sufficient to characterize the cocrystal, as well as by an XRPD pattern substantially similar to FIG. 30.

TABLE 10

| Angle °2θ ± 0.2 °2θ | d value Angstrom | Intensity % |
|---|---|---|
| 8.4 | 10.55 | 100% |
| 10.4 | 8.52 | 29% |
| 12.5 | 7.09 | 3% |
| 13.6 | 6.50 | 24% |
| 14.4 | 6.14 | 21% |
| 15.6 | 5.66 | 11% |
| 16.9 | 5.23 | 22% |
| 17.7 | 500 | 24% |
| 17.9 | 4.94 | 18% |
| 18.6 | 4.75 | 9% |
| 20.1 | 4.41 | 4% |
| 20.6 | 4.31 | 10% |
| 20.9 | 4.25 | 9% |
| 21.7 | 4.09 | 2% |
| 22.0 | 4.03 | 2% |
| 23.9 | 3.72 | 12% |
| 25.0 | 3.55 | 30% |
| 25.7 | 3.46 | 23% |
| 27.1 | 3.29 | 16% |
| 29.0 | 3.08 | 8% |

DSC of Cocrystal 5D

Figure 31:
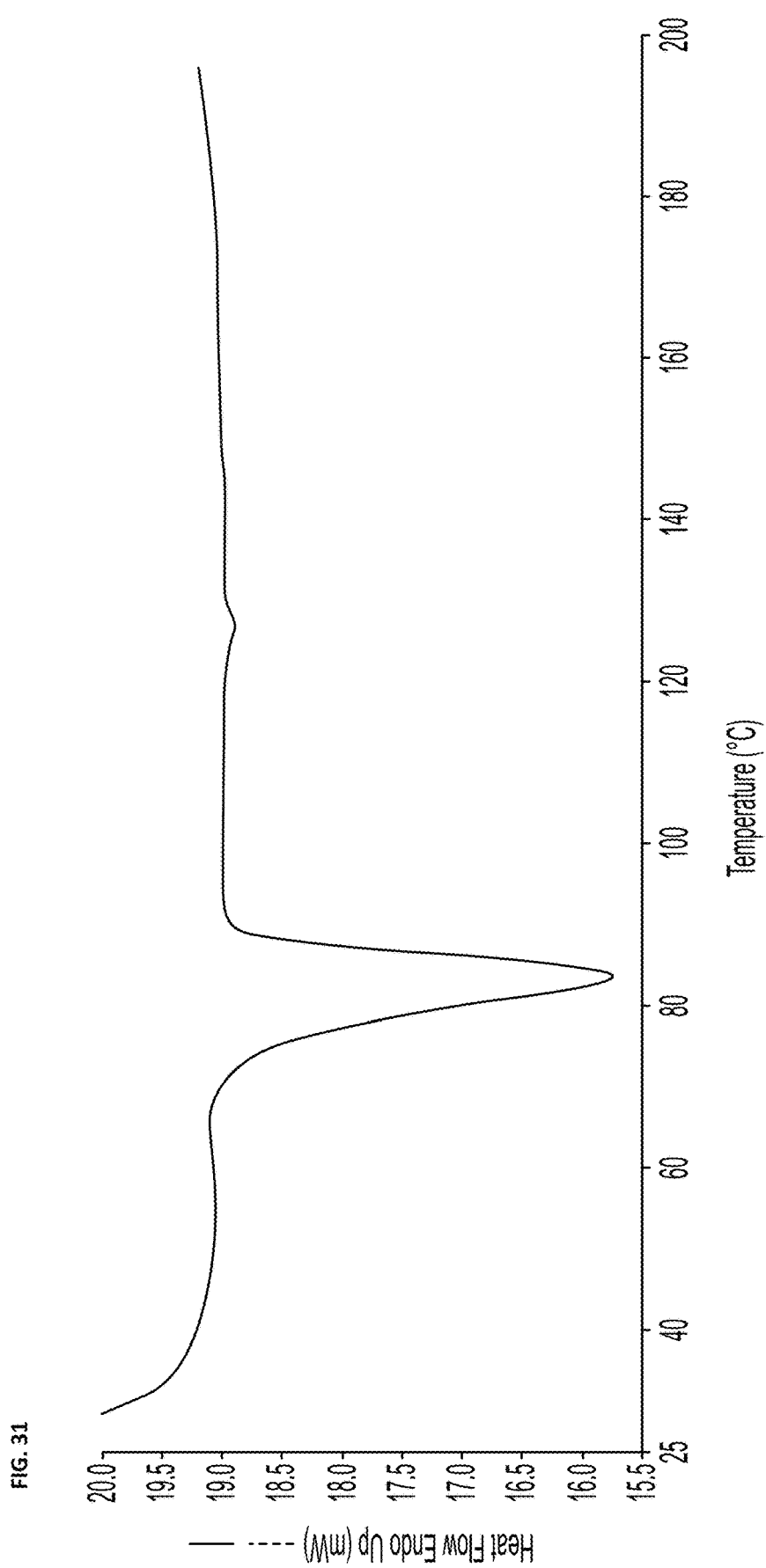
FIG. 31 shows a DSC trace for the 1:1 benzamide gentisic acid cocrystal Form 4 (Cocrystal 5D).

The differential scanning calorimetry (DSC) trace of Cocrystal 5D, FIG. 31, shows a major endotherm with an onset temperature of 75.6° C. and a peak maximum of 83.6° C.

$^1$H NMR Spectrum of Cocrystal 5D

Figure 32:
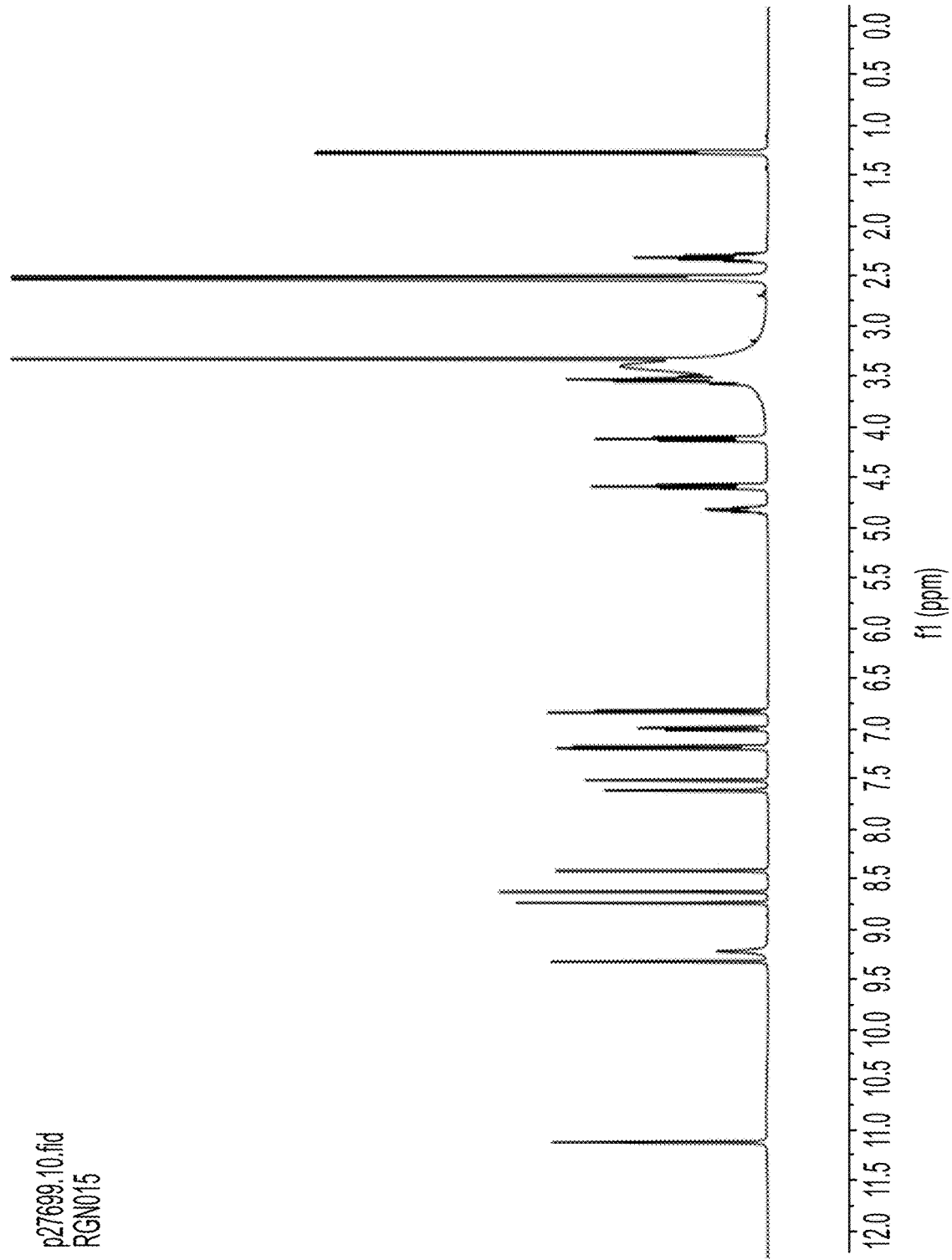
FIG. 32 shows the $^1$H NMR spectrum of 1:1 benzamide gentisic acid cocrystal Form 4 (Cocrystal 5D).

The $^1$H NMR spectrum of Cocrystal 5D, shown in FIG. 32, displays the following peaks: $^1$H NMR (400 MHz, DMSO): δ 1.24-1.26 (3H), 2.27-2.32 (2H), 2.48 (3H), 3.30 (3H), 3.46-3.55 (2H), 4.06-4.12 (2H), 4.52-4.59 (2H), 4.74-4.84 (1H), 6.77-6.79 (1H), 6.94-6.97 (1H), 7.10-7.14 (1H), 7.45-7.49 (1H), 7.55-7.58 (1H), 8.34-8.39 (1H), 8.55-8.59 (1H), 8.66-8.70 (1H), 9.14 (1H), 9.25-9.27 (1H) and 11.05 (1H). The peak at 6.77-6.79 ppm in the $^1$H NMR spectrum corresponds to one proton of gentisic acid. Comparison of the integration of this peak with that at 4.74-4.84, which corresponds to one proton of AZD1656, indicates that the cocrystal has as API:coformer stoichiometry of 1:1.

Example 9: Solid Form Inter-Conversion Study of Cocrystal 5

A study was carried out to assess the potential for the different crystalline forms of Cocrystal 5 to undergo solid form conversion and thus to determine if all forms of Cocrystal 5 can be converted to a single polymorphic form. 50 mg of Cocrystals 5A, 5B, 5C, and 5D were separately slurried at room temperature in 2 mL of nitromethane, acetonitrile or 1:1 (v/v) ethyl acetate/methyl tert-butyl ether for 24 hours. A second set of experiments were carried out where 10 mg each of Cocrystals 5A, 5B, 5C, and 5D were combined and slurried in 2 mL of nitromethane, acetonitrile or 1:1 (v/v) ethyl acetate/methyl tert-butyl ether for 24 hours. After this time all the resulting products were filtered under vacuum and analysed by XRPD. XRPD confirmed that all of the different forms of Cocrystal 5 had been converted to a single polymorphic form, form 5A, in all three solvents examined when either slurried alone or as a combination of forms. This confirms that it is possible to convert all of the different forms of Cocrystal 5 into a single polymorphic form and that Cocrystal 5A is the thermodynamically most stable form of the 1:1 benzamide gentisic acid cocrystal.

Example 10: Solid-State Stability Study for the Benzamide Cocrystals of the Invention A study was carried out to examine the physical stability of the benzamide cocrystals of the invention with respect to solid form conversion or signs of decomposition over time under both ambient and accelerated conditions. 50 mg each of Cocrystal 1, Cocrystal 2, Cocrystal 4, and Cocrystal 5A were separately placed in a sealed container at 40° C. and 75% relative humidity and stored under these conditions for 3 months. After this time all samples remained unchanged in appearance with no signs of deliquescence and no signs of any colour change. Each sample was analysed by XRPD to observe any potential form changes and the results of the study are shown in Table 11.

TABLE 11

| | 40° C./75% RH - 3 months | |
|---|---|---|
| Cocrystal | Appearance | XRPD analysis |
| 1:1 BENZAMIDE FUMARIC ACID | No change | No change (as FIG. 1) |
| 1:1 BENZAMIDE MALEIC ACID | No change | No change (as FIG. 7) |
| 1:1 BENZAMIDE L-TARTARIC ACID HYDRATE | No change | No change (as FIG. 16) |
| 1:1 BENZAMIDE GENTISIC ACID FORM 1 | No change | No change (as FIG. 20) |

A second stability study was carried out where 50 mg each of Cocrystal 1, Cocrystal 2, Cocrystal 3, Cocrystal 4, and Cocrystal 5A were separately placed in a clear glass vial which was then stored under ambient conditions for 12 months. After this time all the cocrystals remained as white solids with no signs of colour change. Each sample was analysed by XRPD to observe any potential form changes and the results of the study are shown in Table 12.

TABLE 12

| | Ambient Conditions - 12 months | |
|---|---|---|
| Cocrystal | Appearance | XRPD analysis |
| 1:1 BENZAMIDE FUMARIC ACID | No change | No change (as FIG. 1) |
| 1:1 BENZAMIDE MALEIC ACID | No change | No change (as FIG. 7) |
| 1:1 BENZAMIDE MALONC ACID | No change | No change (as FIG. 13) |
| 1:1 BENZAMIDE L-TARTARIC ACID HYDRATE | No change | No change (as FIG. 16) |
| 1:1 BENZAMIDE GENTISIC ACID FORM 1 | No change | No change (as FIG. 20) |

It can be seen from Table 12 that after 12-month storage under ambient conditions all of the cocrystals retained their original crystalline form and that none of the benzamide cocrystals of the invention undergo solid form conversion or dissociation under these conditions. The benzamide cocrystals of the invention retained their original polymorphic form under both ambient and accelerated storage conditions.

Example 11: Dry Milling of the Benzamide Cocrystals of the Invention

In order to prepare cocrystal samples of similar particle size for a dissolution study and to assess the impact of milling on the crystallinity of the cocrystals, Cocrystal 1, Cocrystal 2, Cocrystal 3, Cocrystal 4 and Cocrystal 5a were dry milled using a ball mill. WO 2012/007758 discloses that to achieve satisfactory dissolution of the benzamide compound particle size reduction was required. Dry milling of the pure benzamide compound was problematic due to excessive adhesion to the stainless-steel walls of the milling vessel resulting in low recovery yields. Thus, a solid form of the benzamide compound that could undergo particle size reduction with an efficient recovery rate without the need to use a co-milling excipient is beneficial. The milled cocrystals, Cocrystal 1, Cocrystal 2, Cocrystal 3, Cocrystal 4 and Cocrystal 5a, were therefore assessed by eye for any potential agglomeration issues or excessive sticking to the walls of the milling vessel that might indicate potential adhesion/cohesion issues such as those of the pure benzamide compound.

200 mg each of Cocrystal 1, Cocrystal 2, Cocrystal 3, Cocrystal 4 and Cocrystal 5a were separately placed in a 25 ml stainless-steel milling jar containing a 1 cm stainless steel ball bearing. Each benzamide cocrystal of the invention was dry milled in a Retsch MM400 ball mill for 2×15 min at 30 Hz. The product was assessed by eye and by XRPD. None of Cocrystal 1, Cocrystal 2, Cocrystal 3, Cocrystal 4 or Cocrystal 5a showed any signs of loss of crystallinity due to milling. Assessment by eye of each of Cocrystal 1, Cocrystal 2, Cocrystal 3, Cocrystal 4 and Cocrystal 5a indicated that the milled cocrystals all were easily recoverable from the milling chamber with no excessive adhesion to the walls of the milling jar. Also, each of Cocrystal 1, Cocrystal 2, Cocrystal 3, Cocrystal 4 and Cocrystal 5a were obtained as a free-flowing powder with no obvious signs of agglomeration.

Example 12: Dissolution Studies

Dissolution studies will be carried out to compare the rate of dissolution of the benzamide cocrystals of the invention, Cocrystal 1, Cocrystal 2, Cocrystal 3, Cocrystal 4 and Cocrystal 5a, with the pure benzamide compound in both simulated gastric and intestinal media.

The dissolution study will be carried out using 50 ml simulated gastric fluid (FaSSGF) at pH 1.6 (37° C.) or 50 ml simulated intestinal fluid (FaSSIF V2) at pH 6.5 (37° C.) using a quantity of Cocrystal 1, Cocrystal 2, Cocrystal 3, Cocrystal 4, Cocrystal 5a or the pure benzamide compound Form 6 equivalent to 50 mg of the benzamide compound. The dissolution study will be carried out using the Pion inForm© instrument. Detection and quantification of the benzamide compound will be performed by in-situ UV-spectroscopy using a fibre-optic probe, allowing instantaneous data collection from the point of sample introduction. UV absorption data will be converted to mg/ml (±0.2 mg/ml) using a previously determined pH dependent molar extinction coefficient to quantitate the amount of dissolved drug. The dissolution of each of Cocrystal 1, Cocrystal 2, Cocrystal 3, Cocrystal 4 and Cocrystal 5a will be compared with that of the benzamide compound.

The claimed invention is:

1. A 1:1 3-{[5-(azetidine-1-ylcarbonyl) pyrazin-2-yl]oxy}-5-{[(1S)-1-methyl-2-(methyloxy)ethyl]oxy}-N-(5-methylpyrazin-2-yl)benzamide fumaric acid cocrystal.

2. The cocrystal of claim 1, characterized by at least one of:
   a triclinic, P1 crystal system space group at a temperature of 292 (4) K;
   unit cell dimensions a=9.8435 (3) Å, b=11.4054 (3) Å, c=15.0743 (6) Å, α=95.605 (3)°, β=108.628 (3)°, and γ=113.219 (3)°;
   an X-ray powder diffraction pattern having at least three peaks selected from 6.4, 8.7, 14.4, 15.9, 22.2, and 27.3° 2θ±0.2° 2θ; or
   an X-ray powder diffraction pattern substantially similar to FIG. 1.

3. A pharmaceutical composition comprising a therapeutically effective amount of the cocrystal of claim 1 and a pharmaceutically acceptable carrier.

4. A pharmaceutical composition comprising a therapeutically effective amount of the cocrystal of claim 2 and a pharmaceutically acceptable carrier.

5. The pharmaceutical composition of claim 3, wherein the pharmaceutical composition is a solid dosage form.

6. The pharmaceutical composition of claim 4, wherein the pharmaceutical composition is a solid dosage form.

7. The pharmaceutical composition of claim 3, wherein the therapeutically effective amount of the cocrystal is about 100 mg to about 1000 mg.

8. The pharmaceutical composition of claim 4, wherein the therapeutically effective amount of the cocrystal is about 100 mg to about 1000 mg.

9. The pharmaceutical composition of claim 3, wherein the pharmaceutical composition is a topical formulation.

10. The pharmaceutical composition of claim 4, wherein the pharmaceutical composition is a topical formulation.

11. The pharmaceutical composition of claim 3, wherein the pharmaceutical composition is an inhalable formulation.

12. The pharmaceutical composition of claim 4, wherein the pharmaceutical composition is an inhalable formulation.

13. The pharmaceutical composition of claim 3, wherein the pharmaceutical composition is an injectable formulation.

14. The pharmaceutical composition of claim 4, wherein the pharmaceutical composition is an injectable formulation.

* * * * *